(12) United States Patent
Tashiro et al.

(10) Patent No.: US 8,748,659 B2
(45) Date of Patent: Jun. 10, 2014

(54) METHOD FOR PRODUCING ALPHA,BETA-UNSATURATED CARBOXYLIC ACID-N,N-DISUBSTITUTED AMIDE AND METHOD FOR PRODUCING 3-ALKOXYCARBOXYLIC ACID-N,N-DISUBSTITUTED AMIDE

(75) Inventors: Hironori Tashiro, Chiba (JP); Yasushi Shiraki, Chiba (JP); Makoto Kashima, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 218 days.

(21) Appl. No.: 13/266,899

(22) PCT Filed: Apr. 28, 2010

(86) PCT No.: PCT/JP2010/057580
§ 371 (c)(1),
(2), (4) Date: Dec. 1, 2011

(87) PCT Pub. No.: WO2010/126086
PCT Pub. Date: Nov. 4, 2010

(65) Prior Publication Data
US 2012/0088931 A1    Apr. 12, 2012

(30) Foreign Application Priority Data

May 1, 2009   (JP) ................................. 2009-112132
May 1, 2009   (JP) ................................. 2009-112346
May 1, 2009   (JP) ................................. 2009-112347

(51) Int. Cl.
*C07C 231/02*   (2006.01)

(52) U.S. Cl.
USPC ....................................................... 564/138

(58) Field of Classification Search
USPC ....................................................... 564/138
See application file for complete search history.

(56) References Cited

U.S. PATENT DOCUMENTS

| | | | |
|---|---|---|---|
| 1,986,854 A | 1/1935 | Reid | |
| 2,195,974 A | 4/1940 | Reppe et al, | |
| 2,451,436 A | 10/1948 | Erickson | |
| 2,719,177 A | * 9/1955 | Coover, Jr. et al. | 564/138 |
| 3,468,919 A | * 9/1969 | Kilsheimer et al. | 554/69 |
| 3,821,131 A | 6/1974 | Priest et al. | |
| 3,954,749 A | 5/1976 | Priest et al. | |
| 4,011,223 A | 3/1977 | Priest et al. | |
| 4,012,445 A | 3/1977 | Priest et al. | |
| 4,927,919 A | 5/1990 | Yamada et al. | |
| 6,452,030 B1 | 9/2002 | Chosa et al. | |
| 2011/0089020 A1 | 4/2011 | Krull et al. | |

FOREIGN PATENT DOCUMENTS

| | | |
|---|---|---|
| CN | 101293880 A | 10/2008 |
| DE | 2 358 861 | 5/1974 |
| EP | 0 070 425 | 1/1983 |
| GB | 2 102 426 A | 2/1983 |
| GB | 2 248 234 A | 4/1992 |
| JP | 04 154749 | 5/1992 |
| JP | 9-227476 A | 9/1997 |
| JP | 2000 086599 | 3/2000 |
| JP | 2004 250353 | 9/2004 |
| JP | 2004250353 | * 9/2004 |
| JP | 2007 230967 | 9/2007 |
| WO | 2006 075373 | 7/2006 |
| WO | WO 2009/121486 A1 | 10/2009 |

OTHER PUBLICATIONS

International Search Report Issued Jul. 20, 2010 in PCT/JP10/057580 Filed Apr. 28, 2010.
Extended European Search Report issued Oct. 10, 2012 in Patent Application No. 10769784.9.
D. Enjalbert, et al., "Preparation de nouveaux beta-aminoacides a longue chaine et leur conversion en carboxybetaines bicatenaires F-alkylees" Journal of Flourine Chemistry, vol. 92, No. 2, XP004156225A, Feb. 4, 1999, pp. 145-152.
Extended European Search Report issued Oct. 17, 2013 in Patent Application No. 13179855.5.
Extended European Search Report issued Oct. 17, 2013 in Patent Application No. 13179862.1.

* cited by examiner

*Primary Examiner* — Shailendra Kumar
(74) *Attorney, Agent, or Firm* — Oblon, Spivak, McClelland, Maier & Neustadt, L.L.P.

(57) ABSTRACT

The invention is directed to a technique for effectively producing an amide compound suitable for use as a solvent or a detergent on a large scale and at low cost.

9 Claims, 2 Drawing Sheets

METHOD FOR PRODUCING ALPHA,BETA-UNSATURATED CARBOXYLIC ACID-N,N-DISUBSTITUTED AMIDE AND METHOD FOR PRODUCING 3-ALKOXYCARBOXYLIC ACID-N,N-DISUBSTITUTED AMIDE

This application is a 371 of PCT/JP2010/057580, filed Apr. 28, 2010.

TECHNICAL FIELD

The present invention relates to a method for producing an α,β-unsaturated carboxylic acid-N,N-disubstituted amide or a 3-alkoxycarboxylic acid-N,N-disubstituted amide. More particularly, the present invention relates to a method for effectively producing an α,β-unsaturated carboxylic acid-N,N-disubstituted amide, a 3-alkoxycarboxylic acid-N,N-disubstituted amide, or a compound serving as an intermediate of such an amide, from an α,β-unsaturated carboxylic acid serving as a raw material, which is produced on a large, industrial scale.

BACKGROUND ART

Generally, amide compounds can dissolve a variety of compounds and are readily dissolved in water, and thus can be rinsed off with water. Therefore, amide compounds are envisaged to be used as solvents or detergents. For example, amide compounds can be used as a resist-remover, or as a special solvent for a poorly soluble resin such as polyimide or polyamide.

In particular, amide compounds are considered prospective alternative for solvents that are conventionally used frequently, including a halogen-containing solvent, and NMP (N-methylpyrrolidone) or a like solvent, since such a halogen-containing solvent has been reported to pose problems in terms of toxicity and environmental pollution (e.g., ozone layer destruction), and NMP or the like has been reported to have reproductive toxicity.

In consideration that an amide compound is used as a solvent or a detergent, availability of the amide compound at low cost is important. Therefore, demand has arisen for development of a method for effectively producing an amide compound on a large scale and at low cost, the amide compound being suitable for such an application.

For production of an amide compound suitable for use as a solvent or a detergent (e.g., a 3-alkoxycarboxylic acid-N,N-dialkylamide), production of an α,β-unsaturated carboxylic acid-N,N-dialkylamide is an important technique.

Hitherto known methods for producing α,β-unsaturated carboxylic acid-N,N-dialkylamides include, for example, a method for producing N,N-dimethylacrylamide (DMAA) by use of an acrylate ester, the method being disclosed in Patent Document 1, 2, or 3. However, this method firstly requires a step of esterifying acrylic acid and then requires a step of converting the ester group of the resultant ester compound into an amide group. Generally, conversion of an ester group into an amide group requires a polyol compound (e.g., glycerin) serving as a solvent. Therefore, the method requires, after completion of reaction, a step of separating a reaction product from the solvent. The method also requires, after completion of reaction, a step of separating an alcohol released from the ester compound, or an amine compound remaining in the reaction mixture. Thus, the aforementioned DMAA production method requires many steps. In view of production of an amide compound suitable for use as a solvent or a detergent, or an intermediate of the compound, the production method poses problems in terms of yield and cost.

The countercurrent contact method, which is generally employed during various reactions or purification, is known as a technique for yield improvement or effective production. For example, Patent Document 4 discloses a continuous production method for a cyclic formal; Patent Document 5 discloses a method for purifying a carboxylic acid amide; and Patent Document 6 or 7 discloses a method for producing urea.

There has been known a technique for controlling a reaction employing a compound having a double bond, by inhibition of polymerization. For example, Patent Document 8 discloses a method in which a polymerization inhibitor (e.g., a combination of a thermal polymerization inhibitor such as phenothiazine and a compound having a nitroso group) is added directly to a distillation vessel; Patent Document 9 discloses a method in which nitrogen oxide, serving as a gas exhibiting a polymerization inhibition effect, is caused to flow during distillation; Patent Document 10 discloses a method in which a polymerization inhibitor (e.g., an N-nitrosophenylhydroxylamine salt) that generates, through decomposition, multiple components exhibiting a polymerization inhibition effect is added to a vessel or a reflux portion; and Patent Document 11 discloses a method for preventing polymerization of an N-substituted-(meth)acrylamide during distillation thereof, which method does not affect the quality of a final product.

PRIOR ART DOCUMENT

Patent Document

Patent Document 1: U.S. Pat. No. 2,451,436
Patent Document 2: Japanese Patent Application Laid-Open (kokai) No. H04-208258
Patent Document 3: Japanese Patent Application Laid-Open (kokai) No. H06-199752
Patent Document 4: Japanese Patent Application Laid-Open (kokai) No. H11-106382
Patent Document 5: Japanese Patent Application Laid-Open (kokai) No. H09-227476
Patent Document 6: Japanese Patent Application Laid-Open (kokai) No. S63-126857
Patent Document 7: Japanese Patent Application Laid-Open (kokai) No. S62-39560
Patent Document 8: Japanese Patent Application Laid-Open (kokai) No. S49-36607
Patent Document 9: Japanese Patent Application Laid-Open (kokai) No. S59-7147
Patent Document 10: Japanese Patent Publication (kokoku) No. H07-49414
Patent Document 11: Japanese Patent Application Laid-Open (kokai) No. 2004-107279

SUMMARY OF THE INVENTION

Problems to be Solved by the Invention

The present invention has been made in light of the aforementioned situations, and is directed to a technique for effectively producing an amide compound suitable for use as a solvent or a detergent (hereinafter such an amide compound may be referred to as an "amide solvent") on a large scale and at low cost.

For industrially effective production of an amide solvent on a large scale and at low cost, preferably, a production method employing no ester compound is carried out by use of a raw material which is industrially produced on a large scale. From this viewpoint, an amide solvent may be produced through a production method employing an α,β-unsaturated carboxylic acid as a raw material and involving, for example, the following reactions 1 to 4. Specifically, when an α,β-unsaturated carboxylic acid-N,N-disubstituted amide obtained through, for example, the following reactions 1 to 3 is alkoxylated, an amide solvent can be produced at high yield and high purity.

Reaction 1 (amine addition reaction): α,β-unsaturated carboxylic acid+secondary amine→N,N-disubstituted-β-amino acid Reaction 2 (amidation reaction): N,N-disubstituted-β-amino acid+secondary amine→N,N-disubstituted-β-amino acid-N',N'-disubstituted amide Reaction 3 (deamination reaction): N,N-disubstituted-β-amino acid-N',N'-disubstituted amide→α,β-unsaturated carboxylic acid-N,N-disubstituted amide+secondary amine Reaction 4 (alcohol addition reaction): α,β-unsaturated carboxylic acid-N,N-disubstituted amide+alkanol→3-alkoxycarboxylic acid-N,N-disubstituted amide (amide solvent)

However, a series of these reactions poses many problems as described below.

For example, regarding reaction 1, since an α,β-unsaturated carboxylic acid has a double bond and a carboxyl group, reaction between the carboxylic acid and a secondary amine becomes complicated, and difficulty is encountered in producing an N,N-disubstituted-β-amino acid of interest at high yield. Particularly, an α,β-unsaturated carboxylic acid ammonium salt may be generated before production of an N,N-disubstituted-β-amino acid of interest, and the salt may adversely affect production of the N,N-disubstituted-β-amino acid. In addition, when this reaction is carried out on an industrial scale, sufficient attention must be paid to heat of neutralization.

Reaction 2 poses a problem in that this reaction is an equilibrium reaction with a low equilibrium constant. In order to effectively produce a product of interest on a large, industrial scale and at low cost, the equilibrium must be shifted by removing by-produced water from the reaction system. However, removal of water by means of an adsorbent, which is a technique generally employed for a laboratory-scale reaction, is not suited to an industrial-scale reaction. Meanwhile, removal of water through distillation encounters difficulty in shifting the equilibrium, since a secondary amine is easily removed together with water.

Hitherto, there have been reported techniques for effectively removing water or by-products from the reaction system. For example, Patent Document 4 describes a method for producing a cyclic formal with low impurity content through reaction between an alkylene glycol and formaldehyde. In this method, firstly, an alkylene glycol is brought into countercurrent contact with formaldehyde to thereby produce a reaction mixture containing water and a cyclic formal with low unreacted formaldehyde content; subsequently, the reaction mixture is added to and processed with a distillation column to thereby produce a mixture of the cyclic formal and water; and finally, the mixture is added to and processed with an azeotropic distillation column, to thereby produce the cyclic formal at a desired purity. However, this method poses a problem in that it involves complicated steps. In addition, the technique employed in the water removal step (i.e., removal of water from the mixture of the cyclic formal and water through azeotropic distillation) cannot be applied as is to the aforementioned reaction 2.

Patent Document 5 describes a method for producing a high-purity carboxylic acid amide at high yield. In this method, a crude carboxylic acid amide is added to a column-type continuous crystallization apparatus with a temperature gradient; crystals obtained through cooling crystallization are brought into countercurrent contact with a liquid containing the crude carboxylic acid amide; and crystal purification is carried out by repeating a process of crystal melting and recrystallization. However, this technique cannot solve problems involved in the aforementioned reaction 2.

Similar to the case of reaction 2, reaction 3 (decomposition reaction) poses a problem in that this reaction is an equilibrium reaction with a low equilibrium constant. In order to effectively produce a product of interest on a large, industrial scale and at low cost, the equilibrium must be shifted by rapidly separating an α,β-unsaturated carboxylic acid-N,N-disubstituted amide and a secondary amine, which are produced through this reaction. In a conceivable technique for shifting the equilibrium, for example, decomposition reaction is carried out under reduced pressure conditions, and the resultant product is separated in the form of gas. However, when, for example, the product has a low boiling point, difficulty is encountered in liquefying and separating the product only through cooling, and separation of the product must be performed under pressurized conditions. Thus, this technique, in which the product produced under reduced pressure conditions is liquefied under pressurized conditions, is not suited to mass production, due to poor production efficiency, requirement of a large-scale apparatus, and an increase in power consumption.

In view of the foregoing, an object of the present invention is to provide a method for effectively producing an α,β-unsaturated carboxylic acid-N,N-disubstituted amide, a 3-alkoxycarboxylic acid-N,N-disubstituted amide, or a compound serving as an intermediate of such an amide, on a large scale and at low cost.

Means for Solving the Problems

The present inventors have conducted extensive studies and have found that the aforementioned problems can be solved by reactions performed under specific conditions.

Particularly, the present inventors have found that, regarding the aforementioned reaction 1, when an α,β-unsaturated carboxylic acid is reacted with a secondary amine under specific conditions, the conversion of the carboxylic acid can be increased, and an N,N-disubstituted-β-amino acid can be produced at high purity and high yield.

Also, the present inventors have found that, regarding the aforementioned reaction 2, when a high-boiling-point carboxylic acid is reacted with a low-boiling-point amine under specific conditions by utilizing the difference in boiling point among a product of interest, raw materials, and by-products, a carboxylic acid amide can be effectively produced.

Also, the present inventors have found that, regarding the aforementioned reaction 3, when a polymerization inhibitor which inhibits polymerization in vapor phase (hereinafter may be referred to as a "vapor-phase-polymerization inhibitor") and a polymerization inhibitor which inhibits polymerization in liquid phase (hereinafter may be referred to as a "liquid-phase-polymerization inhibitor") are employed, an N,N-disubstituted-β-amino acid-N',N'-disubstituted amide can be decomposed under specific temperature conditions and pressure conditions, and an α,β-unsaturated carboxylic acid-N,N-disubstituted amide can be produced at high yield and high purity.

The present invention has been accomplished on the basis of these findings. Accordingly, the present invention provides:

(1) a method for producing an N,N-disubstituted-β-amino acid, comprising bringing an α,β-unsaturated carboxylic acid to react with a secondary amine, wherein the ratio by mole of the secondary amine to the α,β-unsaturated carboxylic acid (secondary amine/α,β-unsaturated carboxylic acid) is adjusted to 3 to 10, and the reaction is carried out at 10 to 60° C.;

(2) a method for producing an N,N-disubstituted-β-amino acid as described in (1) above, wherein the α,β-unsaturated carboxylic acid is one or more α,β-unsaturated carboxylic acids selected from among acrylic acid, methacrylic acid, and crotonic acid;

(3) a method for producing an N,N-disubstituted-β-amino acid as described in (1) or (2) above, wherein the secondary amine is a secondary amine represented by the following formula (II):

[F1]

(II)

[wherein each of $R^4$ and $R^5$ represents a C1 to C6 saturated hydrocarbon group, and $R^4$ and $R^5$ may bond together to form a C2 to C8 divalent saturated hydrocarbon group];

(4) a method for producing an N,N-disubstituted-β-amino acid as described in any of (1) to (3) above, wherein the α,β-unsaturated carboxylic acid is added at a rate of 3 to 7 mL/minute;

(5) a method for producing a carboxylic acid amide characterized by comprising bringing a carboxylic acid having a boiling point of 150° C. or higher to react with an amine having a boiling point of 90° C. or lower by means of a countercurrent contact system;

(6) a method for producing a carboxylic acid amide as described in (5) above, wherein the reaction between the carboxylic acid and the amine is carried out at 120 to 200° C.;

(7) a method for producing a carboxylic acid amide as described in (5) or (6) above, wherein the reaction between the carboxylic acid and the amine is carried out at a pressure of 0.17 to 0.87 MPa;

(8) a method for producing a carboxylic acid amide as described in any of (5) to (7) above, wherein the reaction between the carboxylic acid and the amine is carried out in the presence of one or more catalysts selected from among alumina, silica-alumina, a cation exchange resin, and zeolite;

(9) a method for producing a carboxylic acid amide as described in any of (5) to (8) above, wherein the carboxylic acid is an N,N-disubstituted-β-amino acid;

(10) a method for producing a carboxylic acid amide as described in (9) above, wherein the N,N-disubstituted-β-amino acid is one or more N,N-disubstituted-β-amino acids selected from among N,N-dimethyl-β-alanine, N,N-diethyl-β-alanine, 2-methyl-N,N-dimethyl-β-alanine, 2-methyl-N,N-diethyl-β-alanine, 3-methyl-N,N-dimethyl-β-alanine, and 3-methyl-N,N-diethyl-β-alanine;

(11) a method for producing a carboxylic acid amide as described in any of (5) to (10) above, wherein the amine is a secondary amine;

(12) a method for producing a carboxylic acid amide as described in (11) above, wherein the secondary amine is one or more secondary amines selected from among dimethylamine, diethylamine, methylethylamine, diisopropylamine, n-butylmethylamine, s-butylmethylamine, t-butylmethylamine, and dipropylamine;

(13) a method for producing an α,β-unsaturated carboxylic acid-N,N-disubstituted amide, characterized by comprising adding a vapor-phase-polymerization inhibitor to an N,N-disubstituted-β-amino acid-N',N'-disubstituted amide in liquid form; decomposing the N,N-disubstituted-β-amino acid-N',N'-disubstituted amide at 200 to 300° C. and at a pressure of 0.15 to 0.95 MPa, to thereby produce an α,β-unsaturated carboxylic acid-N,N-disubstituted amide in vapor form; and adding a liquid-phase-polymerization inhibitor to the α,β-unsaturated carboxylic acid-N,N-disubstituted amide;

(14) a method for producing an α,β-unsaturated carboxylic acid-N,N-disubstituted amide as described in (13) above, wherein the vapor-phase-polymerization inhibitor is one or more polymerization inhibitors selected from among N-nitrosophenylhydroxylamine ammonium salt, N-nitrosophenylhydroxylamine aluminum salt, N-nitrosophenylhydroxylamine zinc salt, and N-nitrosophenylhydroxylamine iron salt; and the liquid-phase-polymerization inhibitor is one or more polymerization inhibitors selected from among copper dithiocarbamate, phenothiazine, hydroquinone, benzoquinone, and hydroquinone monomethyl ether;

(15) a method for producing an α,β-unsaturated carboxylic acid-N,N-disubstituted amide as described in (13) or (14) above, wherein the vapor-phase-polymerization inhibitor is added in an amount of 0.06 to 2 mass % with respect to the N,N-disubstituted-β-amino acid-N',N'-disubstituted amide;

(16) a method for producing an α,β-unsaturated carboxylic acid-N,N-disubstituted amide as described in any of (13) to (15) above, wherein the liquid-phase-polymerization inhibitor is added in an amount of 100 to 10,000 mass ppm with respect to the α,β-unsaturated carboxylic acid-N,N-disubstituted amide;

(17) a method for producing an α,β-unsaturated carboxylic acid-N,N-disubstituted amide as described in any of (13) to (16) above, wherein the N,N-disubstituted-β-amino acid-N',N'-disubstituted amide is decomposed in the presence of one or more solid acid catalysts selected from among alumina, silica-alumina, a cation exchange resin, and zeolite;

(18) a method for producing an α,β-unsaturated carboxylic acid-N,N-disubstituted amide, comprising the following steps I to III:

step I: a step of adding an α,β-unsaturated carboxylic acid to a secondary amine, and allowing reaction of the resultant mixture to proceed under pressurized conditions;

step II: a step of reacting the product produced through step I with a secondary amine by means of a countercurrent contact system; and step III: a step of decomposing the product produced through step II in the presence of a polymerization inhibitor added thereto;

(19) a method for producing an α,β-unsaturated carboxylic acid-N,N-disubstituted amide as described in (18) above, wherein, in step I, the reaction is carried out under such conditions that the ratio by mole of the secondary amine to the α,β-unsaturated carboxylic acid (secondary amine/α,β-unsaturated carboxylic acid) is 3 to 10, and the reaction temperature is 10 to 60° C.;

(20) a method for producing an α,β-unsaturated carboxylic acid-N,N-disubstituted amide as described in (18) or (19) above, wherein the product produced through step I is a carboxylic acid having a boiling point of 150° C. or higher, and the secondary amine employed in step II has a boiling point of 110° C. or lower;

(21) a method for producing an α,β-unsaturated carboxylic acid-N,N-disubstituted amide as described in any of (18) to (20) above, wherein the polymerization inhibitor employed in step III is a vapor-phase-polymerization inhibitor and a liquid-phase-polymerization inhibitor;

(22) a method for producing a 3-alkoxycarboxylic acid-N,N-disubstituted amide, characterized by comprising employing, as a raw material, an N,N-disubstituted-β-amino acid produced through a production method as recited in any of (1) to (4) above;

(23) a method for producing a 3-alkoxycarboxylic acid-N,N-disubstituted amide, characterized by comprising employing, as a raw material, a carboxylic acid amide produced through a production method as recited in any of (5) to (12) above; and (24) a method for producing a 3-alkoxycarboxylic acid-N,N-disubstituted amide, characterized by comprising employing, as a raw material, an α,β-unsaturated carboxylic acid-N,N-disubstituted amide produced through a production method as recited in any of (13) to (21) above.

Effects of the Invention

According to the present invention, there are provided a method for producing an N,N-disubstituted-β-amino acid at high purity and high yield by increasing the conversion of a carboxylic acid employed; a method for effectively producing a carboxylic acid amide from a high-boiling-point carboxylic acid and a low-boiling-point amine; and a method for producing an α,β-unsaturated carboxylic acid-N,N-disubstituted amide at high yield and high purity by decomposing an N,N-disubstituted-β-amino acid-N',N'-disubstituted amide under pressurized conditions.

Through these methods, an α,β-unsaturated carboxylic acid-N,N-disubstituted amide, which is suitable for use in production of an amide solvent, can be effectively produced on a large scale and at low cost.

BEST MODES FOR CARRYING OUT THE INVENTION

The method for producing an α,β-unsaturated carboxylic acid-N,N-disubstituted amide of the present invention employs the following reactions 1 to 3. When an α,β-unsaturated carboxylic acid-N,N-disubstituted amide produced through, for example, the following reactions 1 to 3 is alkoxylated, an amide solvent can be produced at high yield and high purity.

Reaction 1 (amine addition reaction): α,β-unsaturated carboxylic acid+secondary amine→N,N-disubstituted-β-amino acid Reaction 2 (amidation reaction): N,N-disubstituted-β-amino acid+secondary amine→N,N-disubstituted-β-amino acid-N',N'-disubstituted amide Reaction 3 (deamination reaction): N,N-disubstituted-β-amino acid-N',N'-disubstituted amide→α,β-unsaturated carboxylic acid-N,N-disubstituted amide+secondary amine

The respective reactions will next be described.

1. Amine Addition Reaction

In the amine addition reaction of the method of the present invention, an N,N-disubstituted-β-amino acid is produced from an α,β-unsaturated carboxylic acid and a secondary amine.

No particular limitation is imposed on the α,β-unsaturated carboxylic acid employed in the amine addition reaction, and the α,β-unsaturated carboxylic acid may be, for example, a carboxylic acid represented by the following formula (I).

[F2]

(I)

In formula (I), each of $R^1$ to $R^3$ represents a hydrogen atom, a C1 to C10 hydrocarbon group, a C1 to C10 hydrocarbon group substituted by a carboxyl group (hereinafter may be referred to as a "carboxyl-substituted C1 to C10 hydrocarbon group"), or a carboxyl group. As used herein, "carboxyl-substituted C1 to C10 hydrocarbon group" refers to a C1 to C10 hydrocarbon group in which a hydrogen atom(s) is(are) substituted by a carboxyl group(s). The carboxyl-substituted C1 to C10 hydrocarbon group generally has one to three carboxyl groups, preferably one or two carboxyl groups, more preferably one carboxyl group.

The C1 to C10 hydrocarbon group, or the hydrocarbon group of the carboxyl-substituted C1 to C10 hydrocarbon group is preferably a C1 to C8 hydrocarbon group, more preferably a C1 to C6 hydrocarbon group. Examples of the hydrocarbon group include a linear or branched alkyl group, a cycloalkyl group, an aryl group, and a phenyl group. Preferred is an alkyl group or a phenyl group.

From the viewpoint that the α,β-unsaturated carboxylic acid is employed as a raw material for large-scale production of a product of interest, each of $R^1$ to $R^3$ is preferably a hydrogen atom or a C1 to C10 alkyl group, more preferably a hydrogen atom or a C1 to C5 alkyl group, much more preferably a hydrogen atom or a methyl group.

Specific examples of the carboxylic acid represented by formula (I) include acrylic acid, methacrylic acid, crotonic acid, maleic acid, fumaric acid, citraconic acid, itaconic acid, and cinnamic acid. Of these, preferred are acrylic acid, methacrylic acid, and crotonic acid, each of which is suitable for use as a raw material for large-scale production of a product of interest.

No particular limitation is imposed on the secondary amine employed in the amine addition reaction, and the secondary amine may be, for example, a secondary amine represented by the following formula (II).

[F3]

(II)

In formula (II), each of $R^4$ and $R^5$ represents a C1 to C6 saturated hydrocarbon group. When the number of carbon atoms of the hydrocarbon group of $R^4$ or $R^5$ falls within the above range, since the secondary amine is in a liquid form at around room temperature, and does not have an excessively high boiling point (e.g., 110° C. or lower at ambient pressure), the secondary amine is advantageously employed for the amine addition reaction. From this viewpoint, the number of carbon atoms of the hydrocarbon group of $R^4$ or $R^5$ is preferably one to three, more preferably one or two. $R^4$ and $R^5$ may bond together to form a C2 to C6 (preferably C2 to C5, more preferably C4 or C5) divalent saturated hydrocarbon group.

Examples of the saturated hydrocarbon group represented by $R^4$ or $R^5$ in formula (II) include a linear or branched alkyl group, and a cycloalkyl group. A linear or branched alkyl group is preferred, with a linear alkyl group being more preferred.

Examples of the linear or branched alkyl group represented by $R^4$ or $R^5$ include a methyl group, an ethyl group, an n-propyl group, an isopropyl group, an n-butyl group, a sec-butyl group, a tert-butyl group, various pentyl groups, various hexyl groups, various heptyl groups, various octyl groups, various nonyl groups, and various decyl groups. Preferred is a methyl group or an ethyl group.

Examples of the cycloalkyl group represented by $R^4$ or $R^5$ include a cyclopentyl group and a cyclohexyl group.

Examples of the divalent saturated hydrocarbon group formed through bonding between $R^4$ and $R^5$ include a linear or branched alkylene group, and a cycloalkylene group. A linear or branched alkylene group is preferred. The linear or branched alkylene group may be, for example, a divalent group having a structure formed through a process including removal of one hydrogen atom from each of the linear or branched alkyl groups represented by $R^4$ and $R^5$, and bonding of the carbon atoms from which the hydrogen atoms have been removed.

Specific examples of the secondary amine represented by formula (II) include dimethylamine, diethylamine, methylethylamine, diisopropylamine, n-butylmethylamine, s-butylmethylamine, t-butylmethylamine, and dipropylamine. Of these, dimethylamine or diethylamine is preferred, since it has a suitable boiling point.

The aforementioned amine addition reaction is carried out by adding an α,β-unsaturated carboxylic acid to a secondary amine. When such an amine addition reaction is carried out in the presence of an organic solvent or in the absence of a solvent, a salt formed through neutralization reaction between a secondary amine and an α,β-unsaturated carboxylic acid may precipitate in the form of solid, and the solid salt may disturb stirring in a reactor. However, such a problem can be avoided by adding an α,β-unsaturated carboxylic acid to a secondary amine as described above. Specifically, when the amine addition reaction is carried out under such conditions that the amount of a secondary amine exceeds that of an α,β-unsaturated carboxylic acid, a β-amino acid is produced through the addition reaction. Since the thus-produced β-amino acid is in the form of intramolecular salt, even when the reaction is carried out in the presence of an organic solvent or in the absence of a solvent, the reaction product can be prevented from precipitating as a solid.

In the aforementioned amine addition reaction, the ratio by mole of a starting material secondary amine to another starting material α,β-unsaturated carboxylic acid (secondary amine/α,β-unsaturated carboxylic acid) is adjusted to 3 to 10.

In the case where the ratio by mole is less than 3, an α,β-unsaturated carboxylic acid ammonium salt is likely to be produced, and difficulty is encountered in achieving high yield even when the reaction temperature or time is varied. Particularly when water is not employed as a solvent, an ammonium salt may precipitate in the form of solid as described above, resulting in disturbance of stirring and difficulty in performing the reaction reliably. This may cause a problem in terms of safety, or a problem in that polymerization of the α,β-unsaturated carboxylic acid occurs due to an increase in temperature of the reaction system. In contrast, even in the case where the ratio by mole exceeds 10, the amount of a product of interest is not commensurate with an increase in amount of the secondary amine added, which may cause a problem in terms of yield.

From this viewpoint, the ratio by mole is more preferably 4 to 10. When the ratio by mole is 4 or more, a product of interest is produced at higher purity, and the product can be employed as is in the subsequent step (e.g., amidation reaction).

In the aforementioned amine addition reaction, the reaction temperature is 10 to 60° C., preferably 30 to 40° C., from the viewpoints of reaction stability and efficiency. When the reaction temperature is 10° C. or higher, the reaction does not require a longer period of time than necessary, whereas when the reaction temperature is 60° C. or lower, polymerization of the α,β-unsaturated carboxylic acid can be avoided.

In the aforementioned amine addition reaction, heat is generated as a result of neutralization between the α,β-unsaturated carboxylic acid and the secondary amine. However, in this reaction, the α,β-unsaturated carboxylic acid is added to an excess amount of the secondary amine, and therefore the amount of heat generated can be readily regulated by controlling the rate of addition of the α,β-unsaturated carboxylic acid.

Thus, the amount of heat generated through the reaction can be regulated by controlling the aforementioned addition rate. The temperature of the reaction mixture during addition of the α,β-unsaturated carboxylic acid is related not only to the rate of addition of the carboxylic acid, but also to, for example, the heat capacity of the reaction mixture, the shape (surface area) of a reactor employed, or cooling efficiency. Therefore, when reaction conditions are optimized, preferably, the rate of addition of the carboxylic acid is determined by measuring the reaction temperature while performing the reaction by means of a reactor to be actually employed.

For example, when a reactor described in the Examples hereinbelow was employed, the rate of addition of an α,β-unsaturated carboxylic acid was adjusted to 1 to 10 mL/minute, preferably 3 to 7 mL/minute. When the addition rate falls within this range, the reaction can be reliably carried out, and abnormal temperature rise due to heat of neutralization can be avoided. The reaction temperature may be controlled by using, for example, a cooling apparatus or a coolant in combination with the reactor.

In the aforementioned amine addition reaction, no particular limitation is imposed on the method for adding the α,β-unsaturated carboxylic acid, so long as the reaction temperature can be controlled to fall within the aforementioned range. The α,β-unsaturated carboxylic acid can be added continuously or intermittently. From the viewpoint of temperature control, the α,β-unsaturated carboxylic acid is preferably added intermittently, particularly preferably added dropwise.

In the aforementioned amine addition reaction, no particular limitation is imposed on the reaction pressure. However, when the secondary amine employed has a low boiling point, preferably, liquefaction is performed under pressurized conditions.

In the aforementioned amine addition reaction, no particular limitation is imposed on the reaction time. The reaction for producing an N,N-disubstituted-β-amino acid is an exothermic reaction, and completion of the reaction can be known from change in temperature in the reaction system. In experiments performed in the below-described Examples, the reaction was completed about 0.5 hours after dropwise addition of an α,β-unsaturated carboxylic acid. Therefore, conceivably, when stirring is continued for about one hour after completion of dropwise addition of an α,β-unsaturated carboxylic acid, the thus-produced carboxylic acid amide can be employed in the subsequent step.

As described above, in the amine addition reaction of the method of the present invention, there is avoided a problem in that an α,β-unsaturated carboxylic acid ammonium salt precipitates. This is advantageous for achieving uniform reaction and temperature control. Thus, the conversion of the carboxylic acid can be increased, and an N,N-disubstituted-β-amino acid can be produced at high purity and high yield.

Employment of an N,N-disubstituted-β-amino acid produced through the amine addition reaction of the method of the present invention realizes production of an amide solvent at high yield and high purity.

The amide solvent is produced through a method including, for example, the following steps.

(Amidation reaction): N,N-disubstituted-β-amino acid+secondary amine→N,N-disubstituted-β-amino acid-N',N'-disubstituted amide (Deamination reaction): N,N-disubstituted-β-amino acid-N',N'-disubstituted amide→α,β-unsaturated carboxylic acid-N,N-disubstituted amide+secondary amine (Alcohol addition reaction): α,β-unsaturated carboxylic acid-N,N-disubstituted amide+alkanol→3-alkoxycarboxylic acid-N,N-disubstituted amide (amide solvent)

2. Amidation Reaction

In the amidation reaction of the method of the present invention, an amide compound is produced from a high-boiling-point carboxylic acid and a low-boiling-point amine. A characteristic feature of the amidation reaction resides in that a high-boiling-point carboxylic acid is reacted with a low-boiling-point amine by means of a countercurrent contact system. As used herein, "high-boiling-point carboxylic acid" refers to a carboxylic acid having a boiling point of 150° C. or higher, and "low-boiling-point amine" refers to an amine having a boiling point of 90° C. or lower. As used herein, "countercurrent contact system" refers to a reaction performed by means of, for example, an apparatus shown in FIG. 1. In such a countercurrent contact system, specifically, a high-boiling-point carboxylic acid in the form of liquid is fed into a column through the top thereof, and a low-boiling-point amine in the form of vapor is fed into the column through the bottom thereof, followed by allowing reaction to proceed in the column. The thus-produced carboxylic acid amide exists in the form of liquid in the column. The carboxylic acid amide is taken out through an outlet provided at the lower portion of the column, whereas by-produced water is discharged through an outlet provided at the upper portion of the column.

As described above, the high-boiling-point carboxylic acid employed in the amidation reaction of the method of the present invention has a boiling point of 150° C. or higher. Such a carboxylic acid having a boiling point of 150° C. or higher is suitable for use in the countercurrent contact system. From this viewpoint, the boiling point is more preferably 180° C. or higher, particularly preferably 200° C. or higher. No particular limitation is imposed on the maximum boiling point, but the boiling point is generally 250° C. or lower. Preferably, the high-boiling-point carboxylic acid does not solidify under reaction conditions employed, and has a melting point of 150° C. or lower.

No particular limitation is imposed on the high-boiling-point carboxylic acid employed in the amidation reaction of the method of the present invention, so long as it satisfies the aforementioned requirements in terms of boiling point. The high-boiling-point carboxylic acid employed in the amidation reaction may be, for example, an N,N-disubstituted-β-amino acid, or a product produced through the aforementioned amine addition reaction.

Examples of the N,N-disubstituted-β-amino acid include a carboxylic acid represented by the following formula (III).

[F4]

(III)

In formula (III), each of $R^6$ and $R^7$ represents a C1 to C6 saturated hydrocarbon group, and $R^6$ and $R^7$ may bond together to form a C2 to C12 divalent saturated hydrocarbon group. Each of $R^8$ to $R^{10}$ represents a hydrogen atom, a C1 to C10 hydrocarbon group, a carboxyl-substituted C1 to C10 hydrocarbon group, or a carboxyl group.

The C1 to C6 saturated hydrocarbon group is preferably a C1 to C3 saturated hydrocarbon group, and the C2 to C12 divalent saturated hydrocarbon group is preferably a C2 to C8 divalent saturated hydrocarbon group, more preferably a C4 or C5 divalent saturated hydrocarbon group.

Examples of the saturated hydrocarbon group represented by $R^6$ or $R^7$ in formula (III) include a linear or branched alkyl group, and a cycloalkyl group. A linear or branched alkyl group is preferred, with a linear alkyl group being more preferred.

Specific examples of the saturated hydrocarbon group represented by $R^6$ or $R^7$ in formula (III) or examples of preferred ones may be those described above regarding $R^4$ or $R^5$ in formula (II).

The C1 to C10 hydrocarbon group represented by each of $R^8$ to $R^{10}$ in formula (III), or the hydrocarbon group of the carboxyl-substituted C1 to C10 hydrocarbon group represented by each of $R^8$ to $R^{10}$ in formula (III) is preferably a C1 to C8 hydrocarbon group, more preferably a C1 to C6 hydrocarbon group. Examples of the hydrocarbon group include a linear or branched alkyl group, a cycloalkyl group, an aryl group, and a phenyl group. Preferred is an alkyl group or a phenyl group.

Examples of preferred groups represented by each of $R^8$ to $R^{10}$ in formula (III) may be those described above regarding each of $R^1$ to $R^3$ in formula (I).

Specific examples of the carboxylic acid represented by formula (III) include N,N-dimethyl-β-alanine, N,N-diethyl-β-alanine, 2-methyl-N,N-dimethyl-β-alanine, 2-methyl-N, N-diethyl-β-alanine, 3-methyl-N,N-dimethyl-β-alanine, and 3-methyl-N,N-diethyl-β-alanine. Of these, N,N-dimethyl-β-alanine or N,N-diethyl-β-alanine is preferred, since it does not have a methyl side chain and thus exhibits excellent thermal stability.

As described above, the low-boiling-point amine employed in the amidation reaction of the method of the present invention has a boiling point of 90° C. or lower. Such an amine having a boiling point of 90° C. or lower is suitable for use in the countercurrent contact system. From this viewpoint, the boiling point is more preferably 60° C. or lower, particularly preferably 10° C. or lower. No particular limitation is imposed on the minimum boiling point, but the boiling point is generally 0° C. or higher.

No particular limitation is imposed on the low-boiling-point amine employed in the amidation reaction of the method of the present invention, so long as it satisfies the aforementioned requirements in terms of boiling point. The low-boiling-point amine employed may be, for example, a secondary amine. Examples of the secondary amine include an amine represented by the following formula (IV).

[F5]

(IV)

In formula (IV), each of $R^{11}$ and $R^{12}$ represents a C1 to C6 saturated hydrocarbon group, and is preferably a C1 to C3 saturated hydrocarbon group. $R^{11}$ and $R^{12}$ may bond together to form a C2 to C12 (preferably C2 to C8, more preferably C4 or C5) divalent saturated hydrocarbon group.

Examples of the saturated hydrocarbon group represented by $R^{11}$ or $R^{12}$ in formula (IV) include a linear or branched alkyl group, and a cycloalkyl group. A linear or branched alkyl group is preferred, with a linear alkyl group being more preferred.

Examples of the alkyl group represented by $R^{11}$ or $R^{12}$ in formula (IV) include linear or branched alkyl groups. Specific examples include a methyl group, an ethyl group, an n-propyl group, an isopropyl group, an n-butyl group, a sec-butyl group, a tert-butyl group, various pentyl groups, various hexyl groups, various heptyl groups, various octyl groups, various nonyl groups, and various decyl groups. Preferred is a methyl group or an ethyl group.

Examples of the cycloalkyl group represented by $R^{11}$ or $R^{12}$ in formula (IV) include a cyclopentyl group and a cyclohexyl group.

Examples of the divalent saturated hydrocarbon group formed through bonding between $R^{11}$ and $R^{12}$ in formula (IV) include a linear or branched alkylene group, and a cycloalkylene group. A linear or branched alkylene group is preferred. The linear or branched alkylene group may be, for example, a divalent group having a structure formed through a process including removal of one hydrogen atom from each of the linear or branched alkyl groups represented by $R^{11}$ and $R^{12}$, and bonding of the carbon atoms from which the hydrogen atoms have been removed.

Specific examples of the amine represented by formula (IV) include dimethylamine, diethylamine, methylethylamine, diisopropylamine, n-butylmethylamine, s-butylmethylamine, t-butylmethylamine, and dipropylamine. Of these, dimethylamine or diethylamine is preferred, since it has a suitable boiling point.

As described above, in the present invention, the amidation reaction is carried out by means of a countercurrent contact system. Therefore, reaction efficiency can be greatly improved.

Specifically, the amidation reaction is an equilibrium reaction as described below. In order to improve reaction efficiency, the equilibrium must be shifted to the right.

[E1]

Conceivably, removal of by-produced water from the reaction system is an effective technique for improving reaction efficiency. However, removal of water by means of an adsorbent is not suited to industrial-scale production of a carboxylic acid amide. Meanwhile, removal of water through distillation encounters difficulty in shifting the equilibrium, since a low-boiling-point amine is easily removed together with water.

In contrast, in the method of the present invention, a high-boiling-point carboxylic acid in the form of liquid is fed into a reactor through the upper portion thereof, and a low-boiling-point amine in the form of vapor is fed into the reactor through the lower portion thereof, followed by allowing reaction to proceed in the reactor. The thus-produced carboxylic acid amide, which generally has a high boiling point, is recovered through the bottom of the reactor, and by-produced water is discharged in the form of vapor through the top of the reactor. Therefore, the equilibrium can be shifted, and amidation reaction efficiency can be increased.

The aforementioned reaction by means of the countercurrent contact system requires adjustment of reaction conditions. Preferably, the reaction pressure and the reaction temperature satisfy the following requirements (1) to (3):

(1) the pressure and the temperature fall within such ranges that a high-boiling-point carboxylic acid and a carboxylic acid amide (i.e., product of interest) do not vaporize;

(2) the pressure and the temperature fall within such ranges that a low-boiling-point amine does not liquefy; and (3) the pressure and the temperature fall within such ranges that water vaporizes.

Preferred reaction conditions satisfying the aforementioned requirements are as follows. Specifically, the reaction temperature is preferably 120 to 200° C., more preferably 150 to 180° C. The reaction pressure is preferably 0.17 to 0.87 MPa, more preferably 0.3 to 0.6 MPa. As used herein, "pressure" is represented by absolute pressure.

No particular limitation is imposed on the reactor employed for the aforementioned amidation reaction, so long as the reactor has a region where a high-boiling-point carboxylic acid and a low-boiling-point amine come into contact with each other, and the vapor-liquid equilibrium is established. The reactor may have, for example, a structure with increased contact area by trays or fillers. The amidation reaction may employ a catalyst. Examples of the catalyst include alumina such as γ-alumina; silica-alumina such as high-alumina or low-alumina; a cation exchange resin such as Nafion; and zeolite such as mordenite, Y-type zeolite, β-type zeolite, or MFI-type zeolite.

The aforementioned amidation reaction can effectively produce a carboxylic acid amide from a high-boiling-point carboxylic acid and a low-boiling-point amine. Employment of a carboxylic acid amide produced through the amidation reaction realizes production of an amide solvent at high yield and high purity. The amide solvent is produced through a method including, for example, the following steps.

(Deamination reaction): N,N-disubstituted-β-amino acid-N',N'-disubstituted amide→α,β-unsaturated carboxylic acid-N,N-disubstituted amide+secondary amine

(Alcohol addition reaction): α,β-unsaturated carboxylic acid-N,N-disubstituted amide+alkanol→3-alkoxycarboxylic acid-N,N-disubstituted amide (amide solvent)

3. Deamination Reaction

In the deamination reaction of the method of the present invention, an N,N-disubstituted-β-amino acid-N',N'-disubstituted amide is decomposed into an α,β-unsaturated carboxylic acid-N,N-disubstituted amide and a secondary amine. A characteristic feature of the deamination reaction resides in that a vapor-phase-polymerization inhibitor is added to an N,N-disubstituted-β-amino acid-N',N'-disubstituted amide in liquid form; the N,N-disubstituted-β-amino acid-N',N'-disubstituted amide is decomposed at 200 to 300° C. and at a pressure of 0.15 to 0.95 MPa, to thereby produce an α,β-unsaturated carboxylic acid-N,N-disubstituted amide in vapor form; and a liquid-phase-polymerization inhibitor is added to the α,β-unsaturated carboxylic acid-N,N-disubstituted amide in vapor form.

The aforementioned N,N-disubstituted-β-amino acid-N',N'-disubstituted amide is preferably a compound represented by the following formula (V):

[F6]

(wherein each of $R^{13}$ to $R^{16}$ represents a C1 to C6 (preferably C1 to C3) saturated hydrocarbon group; each of $R^{17}$ to $R^{19}$ represents a hydrogen atom, a C1 to C10 (preferably C1 to C6) hydrocarbon group, a carboxyl-substituted C1 to C10 (preferably C1 to C6) hydrocarbon group, or a carboxyl group; $R^{13}$ and $R^{14}$ may bond together to form a C2 to C8 (preferably C4 or C5) divalent saturated hydrocarbon group; and $R^{15}$ and $R^{16}$ may bond together to form a C2 to C8 (preferably C4 or C5) divalent saturated hydrocarbon group).

Examples of the saturated hydrocarbon group represented by each of $R^{13}$ to $R^{16}$ in formula (V) include a linear or branched alkyl group, and a cycloalkyl group. An alkyl group is preferred.

Examples of the hydrocarbon group represented by each of $R^{17}$ to $R^{19}$ in formula (V), or the hydrocarbon group of the carboxyl-substituted hydrocarbon group represented by each of $R^{17}$ to $R^{19}$ in formula (V) include a linear or branched alkyl group, a cycloalkyl group, and an aryl group. Preferred is an alkyl group or a phenyl group.

Examples of the alkyl group represented by each of $R^{13}$ to $R^{19}$ in formula (V) include linear or branched alkyl groups. Specific examples include a methyl group, an ethyl group, an n-propyl group, an isopropyl group, an n-butyl group, a sec-butyl group, a tert-butyl group, various pentyl groups, various hexyl groups, various heptyl groups, various octyl groups, various nonyl groups, and various decyl groups. Preferred is a methyl group or an ethyl group.

Examples of the divalent saturated hydrocarbon group formed through bonding between $R^{13}$ and $R^{14}$ or between $R^{15}$ and $R^{16}$ include a linear or branched alkylene group, and a cycloalkylene group. An alkylene group is preferred. Specific examples of the linear or branched alkylene group formed through bonding between $R^{13}$ and $R^{14}$ or between $R^{15}$ and $R^{16}$ include divalent groups formed from linear or branched alkyl groups represented by each of $R^{13}$ to $R^{16}$.

Specific examples of the N,N-disubstituted-β-amino acid-N',N'-disubstituted amide include 3-N,N-dimethylaminopropiondimethylamide, 3-N,N-diethylaminopropiondiethylamide, 3-N,N-dimethylamino-2-methylpropiondimethylamide, 3-N,N-diethylamino-2-methylpropiondiethylamide, 3-N,N-dimethylaminobutyldimethylamide, and 3-N,N-diethylaminobutyldiethylamide. Preferred is 3-N,N-dimethylaminopropiondimethylamide, 3-N,N-diethylaminopropiondiethylamide, or the like.

No particular limitation is imposed on the aforementioned vapor-phase-polymerization inhibitor, so long as it is used as a polymerization inhibitor for an α,β-unsaturated carboxylic acid-N,N-disubstituted amide in vapor form. The vapor-phase-polymerization inhibitor is preferably a nitroso compound.

Specific examples of the nitroso compound include a nitrosamine compound, a nitrosamine metal salt, a nitrosobenzene compound, a nitrosoxime compound, a nitrosimine compound, a nitrosamide compound, a nitrosourethane compound, a nitrosonaphthol compound, and a nitrosodialkylaminophenol compound.

Examples of the nitrosamine compound include N,N-dimethyl-p-nitrosoaniline, nitrosodiphenylamine, nitrosodimethylamine, nitroso-N,N-diethylamine, N-nitroso-di-N-butylamine, N-nitroso-di-N-n-butyl-4-butanolamine, N-nitroso-diisopropanolamine, N-nitroso-N-ethyl-4-butanolamine, 5-nitroso-8-hydroxyquinoline, and N-nitrosomorpholine.

Examples of the nitrosamine metal salt include NPH (N-nitrosophenylhydroxylamine ammonium salt), N-nitrosophenylhydroxylamine aluminum salt, N-nitrosophenylhydroxylamine zinc salt, and N-nitrosophenylhydroxylamine iron salt.

Examples of the nitrosobenzene compound include nitrosobenzene and 2,4,6-tri-t-butylnitrosobenzene.

Examples of the nitrosoxime compound include 5-nitrosoxime, and nitrosophenone compounds such as iso-nitrosoacetophenone and α-iso-nitrosopropiophenone.

Examples of the nitrosimine compound include N-nitrosoheptamethyleneimine.

Examples of the nitrosamide compound include N-nitroso-N-methyl-p-toluenesulfonamide.

Examples of the nitrosourethane compound include N-nitroso-N-methylurethane and N-nitroso-N-n-propylurethane.

Examples of the nitrosonaphthol compound include 1-nitroso-2-naphthol, 2-nitroso-1-naphthol, 2-nitroso-1-naphthol-3,6-disulfonic acid sodium salt, and 2-nitroso-1-naphthol-4-sulfonic acid.

Examples of the nitrosodialkylaminophenol compound include 2-nitroso-5-diethylaminophenol hydrochloride, 2-nitroso-5-dimethylaminophenol hydrochloride, 5-iso-nitrosobarbituric acid, and 4-nitrosoresorcyl-1-monomethyl ether.

Of these, a nitrosamine metal salt is preferred, and NPH (N-nitrosophenylhydroxylamine ammonium salt) is more preferred, from the viewpoint of availability on an industrial scale.

The amount of the vapor-phase-polymerization inhibitor added is preferably 0.05 to 10 mass % with respect to the N,N-disubstituted-β-amino acid-N',N'-disubstituted amide. When the amount of the vapor-phase-polymerization inhibitor falls within this range, the amount of heavy components formed in the reactor can be reduced to 10 mass % or less of the amount of the N,N-disubstituted-β-amino acid-N',N'-disubstituted amide added. From this viewpoint, the amount of the vapor-phase-polymerization inhibitor added is more preferably 0.5 to 2 mass %. When the amount falls within this range, virtually no heavy components are detected (1 mass % or less).

Decomposition reaction of the N,N-disubstituted-β-amino acid-N',N'-disubstituted amide may be carried out in the presence or absence of a catalyst.

Examples of the catalyst include solid acid catalysts such as alumina, silica-alumina, a cation exchange resin, and zeolite.

Specific examples of alumina include γ-alumina.

Specific examples of silica-alumina include high-alumina and low-alumina.

Specific examples of the cation exchange resin include Nafion.

Specific examples of zeolite include mordenite, Y-type zeolite, β-type zeolite, and MFI-type zeolite.

Of these, alumina or silica-alumina is preferred, alumina is more preferred, and γ-alumina is much more preferred, from the viewpoint of availability on an industrial scale.

Conditions for decomposition reaction of the aforementioned N,N-disubstituted-β-amino acid-N',N'-disubstituted amide are as follows. Specifically, the temperature is 200 to 300° C., preferably 220 to 280° C., and the pressure is 0.15 to 0.95 Mpa, preferably 0.17 to 0.7 Mpa. When the temperature is lower than 200° C., decomposition reaction proceeds insufficiently, and a large amount of unreacted raw material remains in a product of interest (i.e., a temperature condition of lower than 200° C. is not appropriate for the reaction), whereas when the temperature exceeds 300° C., difficulty is encountered in suppressing polymerization of an α,β-carboxylic acid amide (i.e., a product of interest). When the pressure is less than 0.15 Mpa, the reaction temperature must be adjusted to 200° C. or lower as described above, and an incidental facility (e.g., a pressurizer or a cooler) is required for trapping of generated amine gas, which may lead to an increase in product price, whereas when the pressure exceeds 0.95 Mpa, the reaction temperature exceeds 300° C. as described above, polymerization of a product of interest may cause problems, and a large amount of heat is required for heating, which may lead to an increase in product price.

Figure 3:
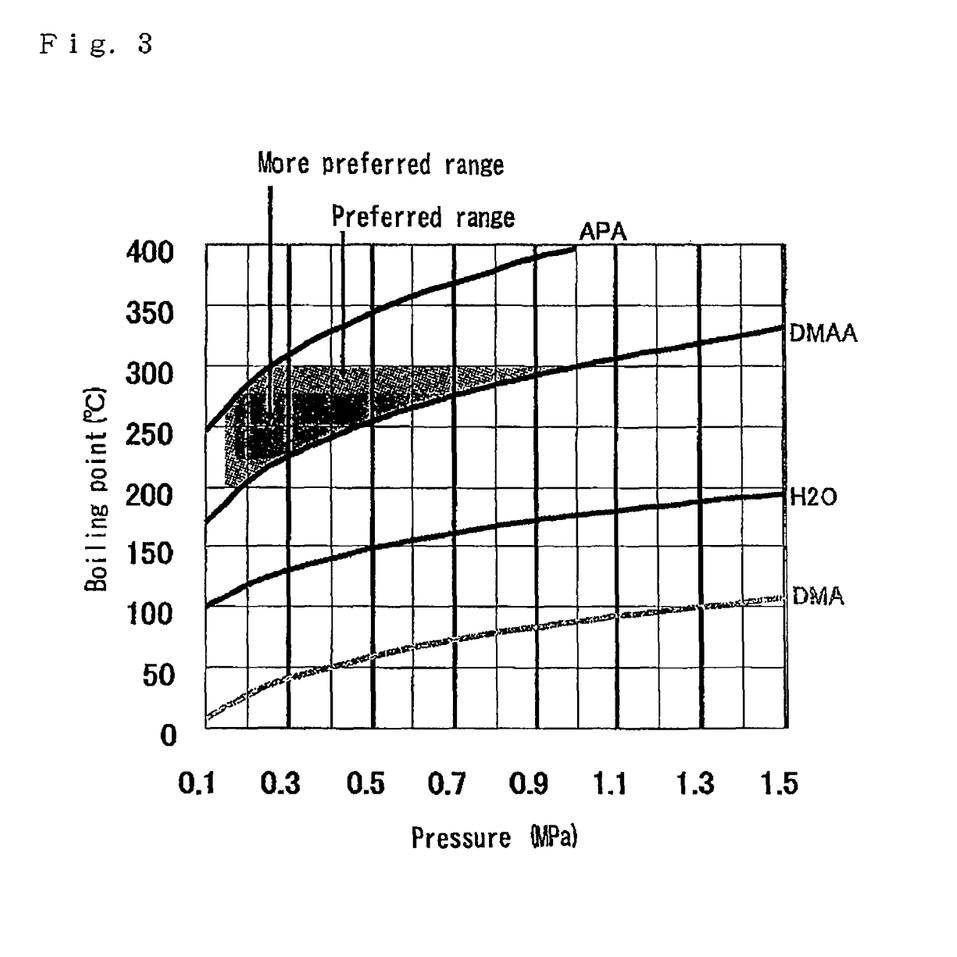
FIG. 3 is a graph showing the relationship between pressure and the boiling point of APA, DMAA, DMA, or water.

FIG. 3 shows the relationship between pressure and the boiling point of 3-dimethylaminopropiondimethylamide (hereinafter may be abbreviated as "APA"), which is an N,N-disubstituted-β-amino acid-N',N'-disubstituted amide as described above, N,N-dimethylacrylamide (hereinafter may be abbreviated as "DMAA"), which is an α,β-unsaturated carboxylic acid-N,N-disubstituted amide as described above, or dimethylamine (hereinafter may be abbreviated as "DMA"), which is a low-boiling-point amine as described below. In FIG. 3, "preferred range" corresponds to a range within which DMAA (i.e., a product of interest) vaporizes without vaporization of APA (i.e., a raw material), and "more preferred range" corresponds to a range within which the product of interest exhibits high purity and thus can be employed as is in the subsequent reaction.

No particular limitation is imposed on the thus-produced α,β-unsaturated carboxylic acid-N,N-disubstituted amide, so long as it is produced through decomposition of the N,N-disubstituted-β-amino acid-N',N'-disubstituted amide. A preferred α,β-unsaturated carboxylic acid-N,N-disubstituted amide exhibits a boiling point of 200 to 250° C. at a pressure of 0.1 to 1.0 MPa. Specific examples of such an α,β-unsaturated carboxylic acid-N,N-disubstituted amide include N,N-dimethylacrylamide, N,N-diethylacrylamide, N,N-dimethylmethacrylamide, N,N-diethylmethacrylamide, N,N-dimethylcrotonamide, and N,N-diethylcrotonamide.

No particular limitation is imposed on the aforementioned liquid-phase-polymerization inhibitor, so long as it is used as a polymerization inhibitor for an α,β-unsaturated carboxylic acid-N,N-disubstituted amide in liquid form. Specific examples of the liquid-phase-polymerization inhibitor include a metal complex, a phenothiazine compound, a hydroquinone compound, and a stable organic radical.

Examples of the metal complex include CEW (copper dithiocarbamate).

Examples of the phenothiazine compound include phenothiazine and methoxyphenothiazine.

Examples of the hydroquinone compound include hydroquinone, benzoquinone, hydroquinone monomethyl ether, catechol, and guaiacol.

Examples of the stable organic radical include diphenylpicrylhydrazyl, α,γ-bisdiphenylene-β-phenylallyl, galvinoxyl, 1,3,5-triphenylverdazyl, di-t-butylnitroxide, 2,2,6,6-tetramethylpiperidine-1-oxyl, 2,2,6,6-tetramethylpiperidone-1-oxyl, 3-carbamoylproxyl, and 2,2,6,6-tetramethyl-4-hydroxypiperidine-1-oxyl (TEMPO).

Of these, a metal complex, a phenothiazine compound, or a hydroquinone compound is preferred, from the viewpoint of availability on an industrial scale. More preferred is copper dithiocarbamate, phenothiazine, methoxyphenothiazine, hydroquinone, benzoquinone, hydroquinone monomethyl ether, catechol, or guaiacol. Much more preferred is copper dithiocarbamate, phenothiazine, hydroquinone, benzoquinone, or hydroquinone monomethyl ether, from the viewpoint of availability on an industrial scale.

The amount of the liquid-phase-polymerization inhibitor added to the produced α,β-unsaturated carboxylic acid-N,N-disubstituted amide is preferably 100 to 10,000 mass ppm with respect to the amide, since, when the amount falls within this range, the amount of heavy components becomes 1% or less the amount of the raw material added. The amount of the liquid-phase-polymerization inhibitor is more preferably 500 to 2,000 mass ppm, since, when the amount falls within this range, virtually no heavy components are detected.

The liquid-phase-polymerization inhibitor is added to an α,β-unsaturated carboxylic acid-N,N-disubstituted amide in liquid or vapor form, the amide being produced through the decomposition reaction. Preferably, the liquid-phase-polymerization inhibitor is added to the α,β-unsaturated carboxylic acid-N,N-disubstituted amide in vapor form. More preferably, a solution of the liquid-phase-polymerization inhibitor is added to the α,β-unsaturated carboxylic acid-N,N-disubstituted amide in vapor form.

According to the method for producing an α,β-unsaturated carboxylic acid-N,N-disubstituted amide of the present invention, a low-boiling-point amine is by-produced through decomposition of the N,N-disubstituted-β-amino acid-N',N'-disubstituted amide. The low-boiling-point amine is preferably an amine having a boiling point of 30° C. or lower, more preferably dimethylamine or diethylamine, much more preferably dimethylamine.

Next will be described an embodiment of the method for producing an α,β-unsaturated carboxylic acid-N,N-disubstituted amide of the present invention in more detail with reference to a drawing.

Figure 2:
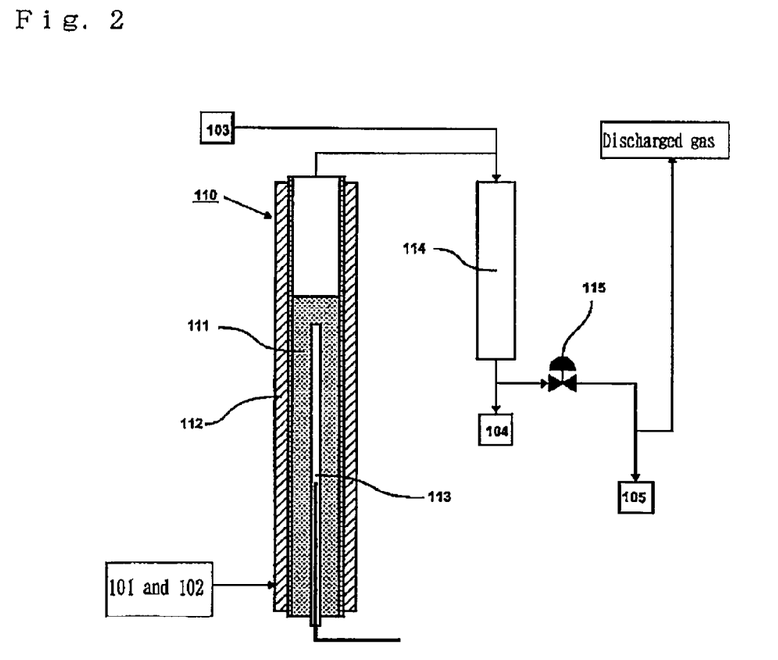
FIG. 2 is a schematic representation of one exemplary production apparatus employed for deamination reaction in the method of the present invention.

In an embodiment of the method for producing an α,β-unsaturated carboxylic acid-N,N-disubstituted amide of the present invention, for example, an apparatus shown in FIG. 2 is employed. Firstly, a mixture of an N,N-disubstituted-β- amino acid-N',N'-disubstituted amide 101 and a vapor-phase-polymerization inhibitor 102 is fed into a vertically held tubular reactor 110 through the lower portion thereof by means of a high-pressure pump. Then, the reactor 110 is hermetically sealed, and the entire reactor is covered with a heating jacket 112 (e.g., a mantle heater or a heat transfer oil jacket). Decomposition reaction may be carried out in the presence or absence of a catalyst 111. When the catalyst 111 is employed, in order to adjust the temperature of a catalytic packed bed to fall within a range of a preset temperature±5° C., preferably, the temperature in the interior of the reactor is measured by means of a temperature sensor 113 so that the interior temperature can be controlled. The pressure conditions for the decomposition reaction can be regulated by means of a pressure regulator 115.

Subsequently, a mixture in vapor form of an α,β-unsaturated carboxylic acid-N,N-disubstituted amide and a low-boiling-point amine produced through the decomposition reaction is fed into a cooler 114, and hot water of about 60° C. is caused to flow through the cooler 114. In this case, an aqueous solution of a liquid-phase-polymerization inhibitor 103 (e.g., hydroquinone) is added to the α,β-unsaturated carboxylic acid-N,N-disubstituted amide. Preferably, the aqueous solution is added to the amide by means of, for example, a high-pressure pump before the amide is fed into the cooler 114. Thus, a product (A) 104 containing an α,β-unsaturated carboxylic acid-N,N-disubstituted amide of interest and water is taken out through an outlet of the cooler 114.

Meanwhile, a product (B) 105 containing a by-produced secondary amine and water may be, for example, collected into a collector provided downstream of the pressure regulator 115 by cooling the collector with dry ice-acetone to about −70° C. or lower.

4. Alcohol Addition Reaction

When the α,β-unsaturated carboxylic acid-N,N-disubstituted amide produced through, for example, the aforementioned reactions 1 to 3 is alkoxylated, an amide solvent can be produced at high yield and high purity.

This reaction is represented as follows.

(Alcohol addition reaction): α,β-unsaturated carboxylic acid-N,N-disubstituted amide+alkanol→3-alkoxycarboxylic acid-N,N-disubstituted amide (amide solvent)

No particular limitation is imposed on the alcohol employed, and it may be appropriately selected in consideration of the purpose. The alcohol may be, for example, a C1 to C10 alcohol, and is preferably a C1 to C6 alcohol. Specific examples include methanol, ethanol, n-propanol, sec-propanol, n-butanol, sec-butanol, t-butanol, n-heptanol, n-hexanol, and cyclohexanol.

As described above, each of the reactions employed in the present invention (i.e., amine addition reaction, amidation reaction, and deamination reaction) contributes to improvement of efficiency or purity. Therefore, when any of these reactions is employed, an α,β-unsaturated carboxylic acid-N,N-disubstituted amide or a 3-alkoxycarboxylic acid-N,N-disubstituted amide can be effectively produced on a large scale and at low cost.

Particularly when, for example, an industrial-scale production is carried out, preferably, these reactions are employed in combination in a series of production steps. For example, there is provided a method for producing an α,β-unsaturated carboxylic acid-N,N-disubstituted amide including the following steps I to III.

Step I: a step of adding an α,β-unsaturated carboxylic acid to a secondary amine, and allowing reaction of the resultant mixture to proceed under pressurized conditions Step II: a step of reacting the product produced through step I with a secondary amine by means of a countercurrent contact system Step III: a step of decomposing the product produced through step II in the presence of a polymerization inhibitor added thereto.

In step I, the reaction is preferably carried out under such conditions that the ratio by mole of a secondary amine to an α,β-unsaturated carboxylic acid (secondary amine/α,β-unsaturated carboxylic acid) is 3 to 10, and the reaction temperature is 10 to 60° C.

The aforementioned technique regarding the amine addition reaction may also be applied to step I.

In step II, the product produced through step I is a carboxylic acid having a boiling point of 150° C. or higher. The secondary amine employed in step II preferably has a boiling point of 110° C. or lower, more preferably 90° C. or lower.

The aforementioned technique regarding the amidation reaction may also be applied to step II.

In step III, the polymerization inhibitor employed is preferably a vapor-phase-polymerization inhibitor and a liquid-phase-polymerization inhibitor.

The aforementioned technique regarding the deamination reaction may also be applied to step III.

EXAMPLES

The present invention will next be described in more detail by way of examples, which should not be construed as limiting the invention thereto.

[Amine Addition Reaction]

Reaction conditions employed in Examples and Comparative Examples are described below. After completion of reaction, the thus-produced liquid (solid in the case of Comparative Example 1) was dissolved in $D_2O$, followed by measurement of $^1$H-NMR (GX-500, product of JEOL Ltd.).

The conversion of a carboxylic acid was determined by use of the following formula.

$$\text{Conversion of carboxylic acid}=1-\text{unreacted carboxylic acid(mol)}/\{\text{unreacted carboxylic acid(mol)}+\text{amine adduct(mol)}\}$$

In this formula, the amount by mole of unreacted carboxylic acid is determined from an NMR signal attributed to a double bond, and the amount by mole of an amine adduct is determined from an NMR signal attributed to methylene or methine.

The purity and yield of an amine adduct were determined by use of the following formulas.

$$\text{Purity of amine adduct}=B/(\text{carboxylic acid added dropwise(mol)}-A)$$

$$\text{Yield of amine adduct}=B/(A+B)$$

A: amount (mol) of a raw material (e.g., acrylic acid) determined from a signal attributed to a double bond of the raw material B: amount (mol) of a product produced through amine addition, the amount being determined from a signal attributed to a methylene chain of the product In Examples and Comparative Examples, there was employed, as a pressure-resistant container, a ϕ60 pressure-resistant container (product of Tokyo Rikakikai Co., Ltd.) having an inner glass container.

Example 1

Reaction Between Dimethylamine and Acrylic Acid

Ratio by Mole of Dimethylamine/Acrylic Acid=3

Dimethylamine (30 g) was added to a pressure-resistant container (reactor), and the reactor was hermetically sealed. The temperature of the reactor was adjusted to 20° C., and acrylic acid (16 g) was fed into the reactor by means of a high-pressure pump. During addition of acrylic acid, heat of neutralization is generated. Therefore, while the reactor was cooled in an ice bath, acrylic acid was added dropwise to the reactor at a rate of 5 to 7 mL/minute, so as to adjust the temperature in the reactor to 25 to 35° C. After completion of dropwise addition, reaction was allowed to proceed for one hour, and then analysis was carried out. The reaction time (as measured from initiation of dropwise addition) was one hour and three minutes.

Example 2

Reaction Between Dimethylamine and Acrylic Acid

Ratio by Mole of Dimethylamine/Acrylic Acid=4

Dimethylamine (30 g) was added to a pressure-resistant container (reactor), and the reactor was hermetically sealed. The temperature of the reactor was adjusted to 20° C., and acrylic acid (12 g) was fed into the reactor by means of a high-pressure pump. During addition of acrylic acid, heat of neutralization is generated. Therefore, while the reactor was cooled in an ice bath, acrylic acid was added dropwise to the reactor at a rate of 5 to 7 mL/minute, so as to adjust the temperature in the reactor to 25 to 35° C. After completion of dropwise addition, reaction was allowed to proceed for one hour, and then analysis was carried out. The reaction time (as measured from initiation of dropwise addition) was one hour and three minutes.

Example 3

Reaction Between Dimethylamine and Acrylic Acid

Ratio by Mole of Dimethylamine/Acrylic Acid=4

Dimethylamine (30 g) was added to a pressure-resistant container (reactor), and the reactor was hermetically sealed. The temperature of the reactor was adjusted to 20° C., and acrylic acid (12 g) was fed into the reactor by means of a high-pressure pump. During addition of acrylic acid, heat of neutralization is generated. Therefore, while the reactor was cooled in an ice bath, acrylic acid was added dropwise to the reactor at a rate of 5 to 7 mL/minute, so as to adjust the temperature in the reactor to 25 to 35° C. Analysis was carried out immediately after completion of dropwise addition (reaction time: three minutes).

Example 4

Reaction Between Dimethylamine and Acrylic Acid

Ratio by Mole of Dimethylamine/Acrylic Acid=4

Dimethylamine (30 g) was added to a pressure-resistant container (reactor), and the reactor was hermetically sealed. The temperature of the reactor was adjusted to 20° C., and acrylic acid (12 g) was fed into the reactor by means of a high-pressure pump. During addition of acrylic acid, heat of neutralization is generated. Therefore, while the reactor was cooled in an ice bath, acrylic acid was added dropwise to the reactor at a rate of 5 to 7 mL/minute, so as to adjust the temperature in the reactor to 25 to 35° C. After completion of dropwise addition, reaction was allowed to proceed for 0.5 hours, and then analysis was carried out. The reaction time (as measured from initiation of dropwise addition) was 33 minutes.

Example 5

Reaction Between Diethylamine and Acrylic Acid

Ratio by Mole of Diethylamine/Acrylic Acid=4

Diethylamine (30 g) was added to a pressure-resistant container (reactor), and the reactor was hermetically sealed. The temperature of the reactor was adjusted to 20° C., and acrylic acid (7.4 g) was fed into the reactor by means of a high-pressure pump. During addition of acrylic acid, heat of neutralization is generated. Therefore, while the reactor was cooled in an ice bath, acrylic acid was added dropwise to the reactor at a rate of 7 to 9 mL/minute, so as to adjust the temperature in the reactor to 25 to 35° C. After completion of dropwise addition, reaction was allowed to proceed for one hour, and then analysis was carried out. The reaction time (as measured from initiation of dropwise addition) was one hour and three minutes.

Example 6

Reaction Between Dimethylamine and Methacrylic Acid

Ratio by Mole of Dimethylamine/Methacrylic Acid=4

Dimethylamine (30 g) was added to a pressure-resistant container (reactor), and the reactor was hermetically sealed. The temperature of the reactor was adjusted to 20° C., and methacrylic acid (14.3 g) was fed into the reactor by means of a high-pressure pump. During addition of methacrylic acid, heat of neutralization is generated. Therefore, while the reactor was cooled in an ice bath, methacrylic acid was added dropwise to the reactor at a rate of 5 to 7 mL/minute, so as to adjust the temperature in the reactor to 25 to 35° C. After completion of dropwise addition, reaction was allowed to proceed for one hour, and then analysis was carried out. The reaction time (as measured from initiation of dropwise addition) was one hour and three minutes.

Example 7

Reaction Between Dimethylamine and Crotonic Acid

Ratio by Mole of Dimethylamine/Crotonic Acid=4

Dimethylamine (30 g) was added to a pressure-resistant container (reactor), and the reactor was hermetically sealed. The temperature of the reactor was adjusted to 20° C., and crotonic acid (14.3 g) was fed into the reactor by means of a high-pressure pump. During addition of crotonic acid, heat of neutralization is generated. Therefore, while the reactor was cooled in an ice bath, crotonic acid was added dropwise to the reactor at a rate of 5 to 7 mL/minute, so as to adjust the temperature in the reactor to 25 to 35° C. After completion of dropwise addition, reaction was allowed to proceed for one hour, and then analysis was carried out. The reaction time (as measured from initiation of dropwise addition) was one hour and three minutes.

Comparative Example 1

Reaction Between Dimethylamine and Acrylic Acid

Ratio by Mole of Dimethylamine/Acrylic Acid=1

Dimethylamine (20 g) was added to a pressure-resistant container (reactor), and the reactor was hermetically sealed. The temperature of the reactor was adjusted to 20° C., and acrylic acid (32 g) was fed into the reactor by means of a high-pressure pump. During addition of acrylic acid, heat of neutralization is generated. Therefore, while the reactor was cooled in an ice bath, acrylic acid was added dropwise to the reactor at a rate of 3 to 5 mL/minute. The temperature in the reactor was maintained at 25 to 35° C. until the amount of acrylic acid added dropwise reached 22 g. However, when acrylic acid was further added dropwise, a solid component was produced, resulting in stopping of stirring. As a result, the temperature in the reactor was elevated and failed to be controlled. Dropwise addition of acrylic acid was continued in this state. After completion of dropwise addition, the reactor was allowed to stand at 30° C. for one hour, and then analysis was carried out. The reaction time (as measured from initiation of dropwise addition) was one hour and eight minutes.

Comparative Example 2

Reaction Between Dimethylamine and Acrylic Acid

Ratio by Mole of Dimethylamine/Acrylic Acid=2

Dimethylamine (30 g) was added to a pressure-resistant container (reactor), and the reactor was hermetically sealed. The temperature of the reactor was adjusted to 20° C., and acrylic acid (24 g) was fed into the reactor by means of a high-pressure pump. During addition of acrylic acid, heat of neutralization is generated. Therefore, while the reactor was cooled in an ice bath, acrylic acid was added dropwise to the reactor at a rate of 5 to 7 mL/minute, so as to adjust the temperature in the reactor to 25 to 35° C. After completion of dropwise addition, reaction was allowed to proceed for one hour, and then analysis was carried out. The reaction time (as measured from initiation of dropwise addition) was one hour and five minutes.

TABLE 1

|  | Examples | | | | | | | Comparative Examples | |
| --- | --- | --- | --- | --- | --- | --- | --- | --- | --- |
|  | 1 | 2 | 3 | 4 | 5 | 6 | 7 | 1 | 2 |
| Conversion of carboxylic acid (%) | 97 | 100 | 90 | 95 | 100 | 98 | 95 | 0 | 66 |
| Purity of amine adduct (%) | 100 | 100 | 100 | 100 | 100 | 100 | 100 | 0 | 100 |
| Yield of amine adduct (%) | 97 | 100 | 90 | 95 | 100 | 98 | 95 | 0 | 66 |

[Amidation Reaction]

The resultant reaction mixture was analyzed through gas chromatography (GC). Analysis conditions are as follows.

Column: HP-1, product of Agilent Technologies, inner diameter: 0.32 mm, length: 60 m, film thickness: 1.00 μm
Oven: 100° C. (0 min)—temperature elevation (15° C./min)—250° C. (10 min)
Carrier gas: helium (35 cm/sec)
Injection: 200° C.
Split ratio: 1:20
Detector: FID (250° C.)
Make-up: nitrogen (30 mL/min)
Amount of sample: 1.0 μL
GC: Agilent 6850 Network GC System
The conversion of DMBA (N,N-dimethyl-β-alanine) was determined by use of the following formula.

Conversion of DMBA=1−DMBA(mol)/(DMBA amide(mol)+DMBA(mol))

No by-products were detected through GC analysis. Conceivably, side reactions producing GC-undetectable by-products (e.g., polymerization) did not occur. Therefore, the amide selectivity in the reaction was regarded as 100%.

Since no by-products were detected through GC analysis, and the mass balance between reactants and products was approximately 100%, the reaction selectivity was regarded as 100%. Therefore, the conversion of DMBA became the same as the yield of an amide.

The results are shown in Table 3.

Production Example 1

Production of Reactor

Figure 1:
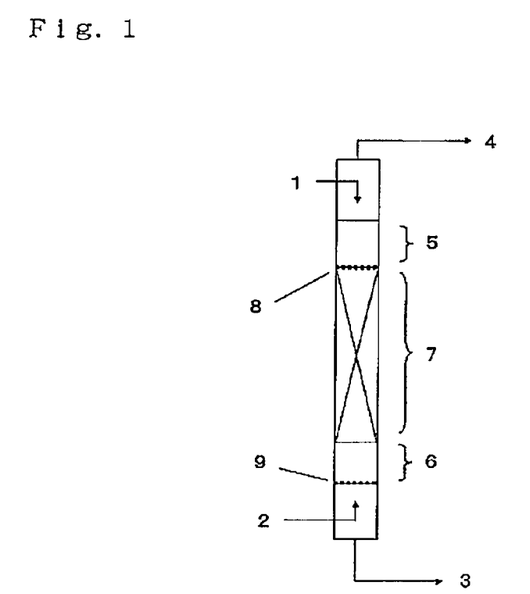
FIG. 1 shows an apparatus for performing a countercurrent contact system.

FIG. 1 shows the structure of a reactor employed in Examples. The reactor was produced through the following method.

A stainless steel tube having a length of 50 cm and an inner diameter of 2.4 cm was vertically held. A stainless steel mesh was provided at the lowermost portion of the tube for preventing falling of a filler. Glass beads having a diameter of 2 mm were placed on the mesh so as to attain a height of 10 cm, and a catalyst (alumina: N611N, product of Nikki Chemical Co., Ltd.) was charged so as to attain a height of 30 cm. A stainless steel mesh was placed on the catalyst, and glass beads having a diameter of 2 mm were placed on the mesh so as to attain a height of 10 cm, followed by hermetic sealing of the tube. In addition, a vapor component outlet was provided, via a pressure regulator, on the upper portion of the reactor, and a liquid component outlet was provided, via a pressure regulator, on the lower portion of the reactor. Furthermore, the entire tube was covered with a heating jacket (a mantle heater or a heat transfer oil jacket) so as to control the temperature of the catalytic packed bed.

Upon actual reaction, a liquid high-boiling-point carboxylic acid was fed into the reactor through the upper portion thereof by means of a high-pressure pump, and a vaporized low-boiling-point amine was fed into the reactor through the lower portion thereof. A carboxylic acid amide (i.e., a product of interest) is taken out through the liquid component outlet provided on the lower portion of the reactor, whereas by-produced water and unreacted low-boiling-point amine are discharged through the vapor component outlet provided on the upper portion of the reactor.

Example 8

In the reactor produced in Production Example 1, the two pressure regulators were operated to achieve a pressure of 0.3

MPa. The reactor was heated to 150° C. DMBA (N,N-dimethyl-β-alanine) was heated to melt at 100° C., and fed into the reactor through the upper portion thereof at a rate of 5 mL/min (330 g/h, 2.82 mol/h). Vaporized DMA (dimethylamine) was pressurized with nitrogen at 0.85 MPa, and fed into the reactor through the lower portion thereof at a rate of 3.1 mL/min (126.5 g/h, 2.81 mol/h) (ratio by mole of DMA/DMBA=1.0). After the elapse of 30 minutes after stabilization of reaction, a product obtained through the liquid component outlet was trapped in 100 mL of methanol, and the product was subjected to GC analysis.

Example 9

The procedure of Example 8 was repeated, except that the feed rate of DMA was changed to 4.7 mL/min (191.8 g/h, 4.15 mol/h) (ratio by mole of DMA/DMBA=1.5).

Example 10

The procedure of Example 8 was repeated, except that the feed rate of DMA was changed to 6.2 mL/min (253.0 g/h, 5.61 mol/h) (ratio by mole of DMA/DMBA=1.99).

Example 11

The procedure of Example 8 was repeated, except that the feed rate of DMA was changed to 9.3 mL/min (379.4 g/h, 8.42 mol/h) (ratio by mole of DMA/DMBA=2.99).

Comparative Examples 3 to 6

Calculation of Equilibrium Constant K

For preparation of a sample, DMBA (1.00 g), 40% aqueous DMA solution (3.85 g), and powdery alumina (N613N, product of Nikki Chemical Co., Ltd.) (1 g) were added to a 15-mL stainless steel pressure-resistant container, and the container was hermetically sealed. Thus, three samples were prepared, and the samples were heated in an oil bath at 150° C. under stirring. The samples were removed every eight hours, and subjected to GC analysis. The results are shown in Table 2. This reaction is represented by the following equilibrium formula. Conceivably, the reaction reaches equilibrium after 24 hours of heating.

DMBA+DMA ⇔ DMBA amide+Water    [E2]

Therefore, the equilibrium conversion under these conditions is 17.2%. Meanwhile, the equilibrium constant K is represented by the following formula.

K=[DMBA amide]×[H$_2$O]/{[DMBA]×[DMA]}

In this formula, the amount of each of the parenthesized components is represented by molarity at equilibrium. Since the sample employed in the present experiment is a uniform solution whose volume does not change, the aforementioned equilibrium constant is obtained by using the amounts by mole of the parenthesized components.

Specifically, when the amounts by mole of the respective components at equilibrium are determined, the equilibrium constant can be calculated. As described above, since the amide selectively in the reaction is 100%, the amounts by mole of the respective components every eight hours can be calculated on the basis of the conversion of DMBA. Table 2 shows the amounts by mole of the respective components.

TABLE 2

| Reaction time (h) | | 0 | 8 | 16 | 24 |
|---|---|---|---|---|---|
| Conversion of DMBA (%) | | 0 | 13.9 | 17.1 | 17.2 |
| Yield of amide (%) | | 0 | 13.9 | 17.1 | 17.2 |
| Amount of | DMBA | 8.5 | 7.3 | 7.1 | 7.1 |
| component (mol) | DMA | 34.1 | 33.0 | 32.7 | 32.7 |
| (calculated value) | H$_2$O | 128.3 | 127.1 | 126.8 | 126.8 |
| | DMBA amide | 0.0 | 1.2 | 1.5 | 1.5 |
| Equilibrium constant | | — | — | — | 0.8062 |

[Calculation of Conversion of DMBA at Respective Raw Material Ratios]

As shown above, in this experiment, the equilibrium constant in the aforementioned equilibrium formula is 0.8062 at 150° C. Equilibrium conversions at different raw material ratios can be calculated by use of the thus-obtained equilibrium constant. Table 3 shows conversions of DMBA in the cases of Comparative Examples 3 to 6 (i.e., raw material ratios are the same as those in the corresponding Examples, and the reaction is carried out without use of a countercurrent contact system).

TABLE 3

| | Examples | | | | Comparative Examples | | | |
|---|---|---|---|---|---|---|---|---|
| | 8 | 9 | 10 | 11 | 3 | 4 | 5 | 6 |
| Ratio by mole (DMA/DMBA) | 1 | 1.5 | 2 | 3 | 1 | 1.5 | 2 | 3 |
| Conversion of DMBA | 94.91 | 98.12 | 99.23 | 99.84 | 47.32 | 56.89 | 63.44 | 71.89 |
| Yield of amide | 94.91 | 98.12 | 99.23 | 99.84 | — | — | — | — |

[Deamination Reaction]

Example 12

Production of N,N-dimethylacrylamide

The apparatus shown in FIG. 2 was employed. The temperature of the reactor was adjusted to 250° C., and the pressure regulator was operated to achieve a pressure of 0.3 MPa. In the reactor (formed of a stainless steel tube having a length of 50 cm and an inner diameter of 2.4 cm), a catalyst (alumina: N611N, product of Nikki Chemical Co., Ltd.) was charged so as to attain a height of 40 cm. A mixture of 3-dimethylaminopropiondimethylamide and 2 mass % NPH (hereinafter the mixture may be referred to as "raw material mixture") was fed into the reactor through an inlet provided on the lower portion of the reactor at a rate of 1 mL/min by means of a high-pressure pump. Subsequently, a gas generated through decomposition reaction and 0.1 mass % aqueous hydroquinone solution (hydroquinone concentration: 1,020 mass ppm on the basis of 3-dimethylaminopropiondimethylamide) were injected into the cooler by means of a high-pressure pump, and hot water of 60° C. was caused to flow through the cooler. Reaction was allowed to proceed for five hours while the pressure was adjusted by means of the pressure regulator, and a product taken out from the cooler (product (A)) was trapped in 100 mL of methanol. A collector for collecting by-products (i.e., dimethylamine and water) was provided downstream of the cooler, and a product (B) was collected by cooling the collector with dry ice-acetone to −70° C. or lower. Injection was stopped, and air was fed into the reactor through the inlet provided on the lower portion thereof, to thereby cool the reactor to 30° C. or lower.

Volatile components of the product (A) were separated by means of an evaporator, weighed, and subjected to gas chromatographic analysis (GC analysis). Since no peaks attributed to by-products were observed, the material other than heavy components (nonvolatile components) was regarded as being converted into N,N-dimethylacrylamide (DMAA) (i.e., a product of interest), and the yield and purity of DMAA were calculated. The results are shown in Table 4.

The amount of dimethylamine (DMA) contained in the product (B) was determined through titration with 0.1 mol/L sulfuric acid standard solution, to thereby calculate the percent recovery of DMA. The results are shown in Table 4.

In addition, the catalyst was removed from the reactor, and the total amount of heavy components deposited on the catalyst and the reactor (i.e., the amount of heavy components in the reactor) was determined. The amount of heavy components in the reactor was calculated on the basis of the mass of 3-dimethylaminopropiondimethylamide employed for the reaction. The results are shown in Table 4.

The aforementioned GC analysis was carried out under the following conditions.

Column: HP-1, product of Agilent Technologies, inner diameter: 0.32 mm, length: 60 m, film thickness: 1.00 μm Oven: 100° C. (0 min)—temperature elevation (15° C./min)—250° C. (10 min)

Carrier gas: helium (35 cm/sec)

Injection: 200° C.

Split ratio: 1:20

Detector: FID (250° C.)

Make-up: nitrogen (30 mL/min)

Amount of sample: 1.0 μL

GC: Agilent 6850 Network GC System

The yield of DMAA, the amount of heavy components in the reactor, the amount of heavy components in the product (A), the percent recovery of DMA, and the purity of DMAA were calculated as described below.

Yield of DMAA (mol %)=the amount (mol) of DMAA contained in the product (A) as determined through GC analysis/the amount (mol) of 3-dimethylaminopropiondimethylamide employed as the raw material Amount of heavy components in the reactor(mass %)=the mass of heavy components deposited on the catalyst and the reactor/the mass of 3-dimethylaminopropiondimethylamide employed as the raw material Amount of heavy components in the product(A)(mass %)=the mass of heavy components separated from the product(A)/the mass of 3-dimethylaminopropiondimethylamide employed as the raw material Percent recovery of DMA(mol %)=the amount(mol)of DMA contained in the product(B)as determined through titration/the amount(mol)of 3-dimethylaminopropiondimethylamide employed as the raw material Purity of DMAA(mass %)=the mass of DMAA contained in the product(A)as determined through GC analysis/the mass of the product(A)(exclusive of methanol)

Example 13

Production of N,N-dimethylacrylamide

The procedure of Example 12 was repeated, except that the temperature of the reactor was adjusted to 300° C., and the pressure regulator was operated to achieve a pressure of 0.6 MPa, to thereby produce N,N-dimethylacrylamide.

The yield and purity of DMAA, the amount of heavy components in the product (A), the percent recovery of DMA, and the amount of heavy components in the reactor were determined in the same manner as in Example 12. The results are shown in Table 4.

Example 14

The procedure of Example 12 was repeated, except that the temperature of the reactor was adjusted to 200° C., and the pressure regulator was operated to achieve a pressure of 0.18 MPa, to thereby produce N,N-dimethylacrylamide.

The yield and purity of DMAA, the amount of heavy components in the product (A), the percent recovery of DMA, and the amount of heavy components in the reactor were determined in the same manner as in Example 12. The results are shown in Table 4.

Example 15

The procedure of Example 12 was repeated, except that the amount of NPH was changed to 0.2 mass %, and the concentration of the aqueous hydroquinone solution injected was changed to 0.05 mass % (hydroquinone concentration: 510 mass ppm on the basis of 3-dimethylaminopropiondimethylamide), to thereby produce N,N-dimethylacrylamide.

The yield and purity of DMAA, the amount of heavy components in the product (A), the percent recovery of DMA, and the amount of heavy components in the reactor were determined in the same manner as in Example 12. The results are shown in Table 4.

Example 16

The procedure of Example 12 was repeated, except that the temperature of the reactor was adjusted to 225° C., and the pressure regulator was operated to achieve a pressure of 0.25 MPa, to thereby produce N,N-dimethylacrylamide.

The yield and purity of DMAA, the amount of heavy components in the product (A), the percent recovery of DMA, and the amount of heavy components in the reactor were determined in the same manner as in Example 12. The results are shown in Table 4.

Example 17

The procedure of Example 12 was repeated, except that the amount of NPH was changed to 0.05 mass %, and the concentration of the aqueous hydroquinone solution injected was changed to 0.5 mass % (hydroquinone concentration: 510 weight ppm on the basis of 3-dimethylaminopropiondimethylamide), to thereby produce N,N-dimethylacrylamide.

The yield and purity of DMAA, the amount of heavy components in the product (A), the percent recovery of DMA, and the amount of heavy components in the reactor were determined in the same manner as in Example 12. The results are shown in Table 4.

Comparative Example 7

The procedure of Example 12 was repeated, except that NPH was not added to 3-dimethylaminopropiondimethylamide, and the aqueous hydroquinone solution was replaced with water (hydroquinone concentration: 0 mass ppm on the basis of 3-dimethylaminopropiondimethylamide), to thereby produce N,N-dimethylacrylamide.

The yield and purity of DMAA, the amount of heavy components in the product (A), the percent recovery of DMA, and the amount of heavy components in the reactor were determined in the same manner as in Example 12. The results are shown in Table 4.

Comparative Example 8

The procedure of Example 12 was repeated, except that the temperature of the reactor was adjusted to 200° C., and the pressure regulator was operated to achieve a pressure of 0.1 MPa (ambient pressure), to thereby produce N,N-dimethylacrylamide.

The yield and purity of DMAA, the amount of heavy components in the product (A), the percent recovery of DMA, and the amount of heavy components in the reactor were determined in the same manner as in Example 12. The results are shown in Table 4.

Comparative Example 9

The procedure of Example 12 was repeated, except that the temperature of the reactor was adjusted to 250° C., and the pressure regulator was operated to achieve a pressure of 0.1 MPa (ambient pressure), to thereby produce N,N-dimethylacrylamide.

The yield and purity of DMAA, the amount of heavy components in the product (A), the percent recovery of DMA, and the amount of heavy components in the reactor were determined in the same manner as in Example 12. The results are shown in Table 4.

TABLE 4

|  | Examples | | | | | | Comparative Examples | | |
| --- | --- | --- | --- | --- | --- | --- | --- | --- | --- |
|  | 12 | 13 | 14 | 15 | 16 | 17 | 7 | 8 | 9 |
| Yield of DMAA (mol %) | 99 | 90 | 80 | 95 | 91 | 51 | 34 | 25 | 5 |
| Amount of heavy components in reactor (mass %) | <1 | 8 | 17 | 2 | <1 | 18 | 21 | 70 | <1 |
| Amount of heavy components in product (A) (mass %) | 0 | 1 | <1 | 2 | <1 | 29 | 45 | <1 | <1 |
| Percent recovery of DMA (mol %) | 100 | 90 | 80 | 93 | 89 | 96 | 94 | 25 | 5 |
| Purity of DMAA (mass %) | 100 | 99 | 99 | 98 | 99 | 64 | 43 | 96 | — |

Conceivably, in Comparative Example 9, the reaction did not proceed, and the raw material was only distilled out of the reactor.

As is clear from the aforementioned data of Examples 12 to 17, when the reaction temperature is 200 to 300° C., and the reaction pressure is 0.16 to 0.45 MPa, the decomposition reaction effectively proceeds, and DMAA is produced at high yield and high purity with reduced production of heavy components. In addition, since the reaction is carried out under positive pressure, the percent recovery of DMA is satisfactory, and the amount by mole of recovered DMA is equal to that of the decomposed raw material.

In contrast, in Comparative Example 7 (without use of a polymerization inhibitor), the decomposition reaction proceeds, but production of heavy components is pronounced, and the yield of DMAA is low. Similarly, in Comparative Example 8 or 9 (decomposition reaction at ambient pressure), the yield of DMAA is low.

As shown above, according to the present invention, an N,N-disubstituted-β-amino acid-N',N'-disubstituted amide is effectively decomposed into corresponding α,β-unsaturated amide and secondary amine without requiring negative pressure.

[Production of 3-alkoxy-N,N-dimethylpropionamide from dimethylamine and methacrylic acid Serving as Starting Materials]

Examples 18 to 21

(1) Production of DMBA (N,N-dimethyl-β-alanine)

Dimethylamine (300 g) was added to a pressure-resistant container (reactor), and the reactor was hermetically sealed. The temperature of the reactor was adjusted to 20° C., and methacrylic acid (143 g) was fed into the reactor through one inlet by means of a high-pressure pump. During addition of methacrylic acid, heat of neutralization is generated. Therefore, while the reactor was cooled in an ice bath, methacrylic acid was added dropwise to the reactor at a rate of 10 to 30 mL/minute, so as to adjust the temperature in the reactor to 25 to 35° C. After completion of dropwise addition, reaction was allowed to proceed for one hour.

After completion of reaction, the reactor was depressurized. Thereafter, the reactor was slightly pressurized with nitrogen gas and then depressurized. This process was carried out thrice to thereby remove unreacted dimethylamine gas.

A reaction product (white solid) (229.0 g) was recovered from the reactor. The white solid was subjected to GC analysis and identified as DMBA (purity: 99.95%).

This reaction was carried out repeatedly (20 batches) under the same conditions, to thereby produce DMBA (total amount: 4.57 kg). The average amount of DMBA produced per batch was found to be 228.6 g (yield: 99.8%, purity: 99.92%).

(2) Production of 3-dimethylaminopropiondimethylamide

The reactor produced in Production Example 1 was employed.

In the reactor, the two pressure regulators were operated to achieve a pressure of 0.3 MPa. The reactor was heated to 150° C. The DMBA (N,N-dimethyl-β-alanine) synthesized in (1) above was heated to melt at 100° C., and fed into the reactor through the upper portion thereof at a rate of 5 mL/min (330 g/h, 2.89 mol/h). Vaporized DMA (dimethylamine) was pressurized with nitrogen at 0.85 MPa, and fed into the reactor through the lower portion thereof at a rate of 3.2 mL/min (130.2 g/h, 2.89 mol/h) (ratio by mole of DMA/DMBA=1.0). The temperature in the respective portions of the reactor was stabilized about one hour after initiation of the reaction. Then, the reactor was further operated for one hour for stabilization of the reaction system. Thereafter, a reaction product (transparent liquid) produced through two-hour reaction was collected through the liquid component outlet (639 g).

This liquid was subjected to GC analysis and identified as 3-dimethylaminopropiondimethylamide (purity: 99.8%).

(3) Production of N,N-dimethylacrylamide

The reactor described in Example 12 was employed.

A mixture of 3-dimethylaminopropiondimethylamide and 2 mass % NPH (hereinafter the mixture may be referred to as "raw material mixture") was fed into the reactor through the inlet provided on the lower portion of the reactor at a rate of 1 mL/min by means of a high-pressure pump. Subsequently, a gas generated through decomposition reaction and 0.1 mass % aqueous hydroquinone solution (hydroquinone concentration: 1,020 mass ppm on the basis of 3-dimethylaminopropiondimethylamide) were injected into the cooler by means of a high-pressure pump, and hot water of 60° C. was caused to flow through the cooler. Reaction was allowed to proceed for five hours while the pressure was adjusted by means of the pressure regulator (the amount of the mixture of 3-dimethylaminopropiondimethylamide and 2 mass % NPH fed: 300 g).

A product (382 g) taken out from the cooler was trapped in 100 mL of methanol.

The thus-produced product was subjected to purification treatment by means of a distillation apparatus including a column having 10 trays. As described below, purification was carried out through two methods under different conditions.

[Purification Treatment 1]

The product obtained from the cooler (150 g) was subjected to distillation.

In this distillation, firstly, the pressure in the distillation system was reduced to 50 mmHg, and the temperature of the bottom of the column was gradually elevated from room temperature to 70° C., to thereby remove methanol and water through distillation. At this time, the reflux ratio (R/D) was adjusted to 0/1. Thereafter, the pressure in the system was reduced to 20 mmHg, and distillation was carried out while the temperature of the bottom was regulated at a reflux ratio (R/D) of 1/1. The product obtained until the temperature of the top of the distillation column had reached 80° C. was collected as an initial distillate, and the product obtained after the top temperature had reached 80° C. was collected as a main distillate.

The results of distillation are shown in Table 5.

TABLE 5

| Components | Light components | Initial distillate | Main distillate | Bottom liquid |
|---|---|---|---|---|
| Pressure (mmHg) | 50 | 20 | 20 | — |
| Reflux ratio (R/D) | 0/1 | 1/2 | 1/2 | — |
| Top temperature (° C.) | 20 to 60 | 20 to 80 | 80 to 81 | — |
| Amount (g) | 33.9 | 10.5 | 69.4 | 32.5 |
| GC purity (%) as N,N-dimethylacrylamide | — | 89.8 | 99.7 | 98.5 |

[Purification Treatment 2]

The product obtained from the cooler (150 g) was subjected to distillation.

In this distillation, firstly, the pressure in the distillation system was reduced to 50 mmHg, and the temperature of the bottom of the column was gradually elevated from room temperature to 70° C., to thereby remove methanol and water through distillation. At this time, the reflux ratio (R/D) was adjusted to 0/1. Thereafter, the pressure in the system was reduced to 20 mmHg, and distillation was carried out while the temperature of the bottom was regulated at a reflux ratio (R/D) of 1/1. Distillation was stopped at the time when the temperature of the top of the distillation column reached 80° C., and a bottom liquid (105.3 g) was obtained.

The bottom liquid was subjected to GC analysis and identified as N,N-dimethylacrylamide (purity: 99.1%).

(4) Production of 3-alkoxy-N,N-dimethylpropionamide

[Production of 3-methoxy-N,N-dimethylpropionamide from N,N-dimethylacrylamide Obtained Through Purification Treatment 1 (Example 18)]

N,N-Dimethylacrylamide obtained through purification treatment 1 (30.00 g, 0.302 mol) and methanol (14.50 g, 0.453 mol) were added to a 100-mL three-neck flask equipped with a stirrer, a thermocouple, and a nitrogen gas feed tube. Nitrogen gas was fed into the flask, and a methanol solution (3 mL) containing sodium methoxide (0.163 g, 0.00302 mol) was added to the flask at room temperature under stirring. During addition of the solution, the temperature of the reaction mixture is elevated. Therefore, the temperature in the flask was adjusted to 30 to 40° C. by means of a water bath, and reaction was allowed to proceed for five hours, followed by neutralization with acetic acid.

Unreacted matter was removed by means of an evaporator, and then a product (37.9 g) was obtained through distillation at 133 Pa and 58° C. The product was subjected to GC analysis and identified as 3-methoxy-N,N-dimethylpropionamide (purity: 99.2%).

[Production of 3-methoxy-N,N-dimethylpropionamide from N,N-dimethylacrylamide Obtained Through Purification Treatment 2 (Example 19)]

N,N-Dimethylacrylamide obtained through purification treatment 2 (30.00 g, 0.300 mol) and methanol (14.41 g, 0.450 mol) were added to a 100-mL three-neck flask equipped with a stirrer, a thermocouple, and a nitrogen gas feed tube. Nitrogen gas was fed into the flask, and a methanol solution (3 mL) containing sodium methoxide (0.162 g, 0.00300 mol) was gradually added to the flask at room temperature under stirring. During addition of the solution, the temperature of the reaction mixture is elevated. Therefore, the temperature in the flask was adjusted to 30 to 40° C. by means of a water bath, and reaction was allowed to proceed for five hours, followed by neutralization with acetic acid.

Unreacted matter was removed by means of an evaporator, and then a product (35.7 g) was obtained through distillation at 133 Pa and 58° C. The product was subjected to GC analysis and identified as 3-methoxy-N,N-dimethylpropionamide (purity: 98.9%).

[Production of 3-butoxy-N,N-dimethylpropionamide from N,N-dimethylacrylamide Obtained Through Purification Treatment 1 (Example 20)]

N,N-Dimethylacrylamide obtained through purification treatment 1 (30.00 g, 0.302 mol) and butanol (33.54 g, 0.453 mol) were added to a 100-mL three-neck flask equipped with a stirrer, a thermocouple, and a nitrogen gas feed tube. Nitrogen gas was fed into the flask, and a butanol solution (3 mL) containing sodium methoxide (0.163 g, 0.00302 mol) was gradually added to the flask at room temperature under stirring. During addition of the solution, the temperature of the reaction mixture is elevated. Therefore, the temperature in the flask was adjusted to 30 to 40° C. by means of a water bath, and reaction was allowed to proceed for five hours, followed by neutralization with acetic acid.

Unreacted matter was removed by means of an evaporator, and then a product (48.4 g) was obtained through distillation at 133 Pa and 78° C. The product was subjected to GC analysis and identified as 3-butoxy-N,N-dimethylpropionamide (purity: 99.3%).

[Production of 3-butoxy-N,N-dimethylpropionamide from N,N-dimethylacrylamide Obtained Through Purification Treatment 2 (Example 21)]

N,N-Dimethylacrylamide obtained through purification treatment 2 (30.00 g, 0.300 mol) and butanol (33.34 g, 0.450 mol) were added to a 100-mL three-neck flask equipped with a stirrer, a thermocouple, and a nitrogen gas feed tube. Nitrogen gas was fed into the flask, and a butanol solution (3 mL) containing sodium methoxide (0.162 g, 0.00300 mol) was gradually added to the flask at room temperature under stirring. During addition of the solution, the temperature of the reaction mixture is elevated. Therefore, the temperature in the flask was adjusted to 30 to 40° C. by means of a water bath, and reaction was allowed to proceed for five hours, followed by neutralization with acetic acid.

Unreacted matter was removed by means of an evaporator, and then a product (46.7 g) was obtained through distillation at 133 Pa and 78° C. The product was subjected to GC analysis and identified as 3-butoxy-N,N-dimethylpropionamide (purity: 99.5%).

INDUSTRIAL APPLICABILITY

According to the present invention, an amide compound suitable for use as a solvent or a detergent can be effectively produced on a large scale and at low cost from an $\alpha,\beta$-unsaturated carboxylic acid which is produced on a large, industrial scale.

DESCRIPTION OF REFERENCE NUMERALS

1: High-boiling-point carboxylic acid
2: Low-boiling-point amine
3: Product (carboxylic acid amide)
4: Low-boiling-point amine+water
5: Glass beads
6: Glass beads
7: Catalyst
8: Mesh
9: Mesh
101: N,N-disubstituted-$\beta$-amino acid-N',N'-disubstituted amide
102: Vapor-phase-polymerization inhibitor
103: Liquid-phase-polymerization inhibitor
104: Product (A)
105: Product (B)
110: Reactor
111: Catalyst
112: Heating jacket
113: Temperature sensor
114: Cooler
115: Pressure regulator

The invention claimed is:

1. A method for producing a carboxylic acid amide, the method comprising:
   feeding (i) a carboxylic acid having a boiling point of 150° C. or higher in the form of a liquid into a column of a countercurrent contact system through the top thereof,
   feeding (ii) an amine having a boiling point of 90° C. or lower in the form of a vapor into the column of the countercurrent contact system through the bottom thereof, and
   reacting (i) the carboxylic acid with (ii) the amine in the countercurrent contact system.

2. The method of claim 1, wherein the reacting is carried out at 120 to 200° C.

3. The method of claim 1, wherein the reacting is carried out at a pressure of 0.17 to 0.87 MPa.

4. The method claim 1, wherein the reacting is carried out in the presence of at least one catalyst selected from the group consisting of alumina, silica-alumina, a cation exchange resin, and zeolite.

5. The method of claim 1, wherein the carboxylic acid comprises an N,N-disubstituted-$\beta$-amino acid.

6. The method of claim 5, wherein the N,N-disubstituted-$\beta$-amino acid comprises at least one N,N-disubstituted-$\beta$-amino acid selected from the group consisting of N,N-dimethyl-$\beta$-alanine, N,N-diethyl-$\beta$-alanine, 2-methyl-N,N-dimethyl-$\beta$-alanine, 2-methyl-N,N-diethyl-$\beta$-alanine, 3-methyl-N,N-dimethyl-$\beta$-alanine, and 3-methyl-N,N-diethyl-$\beta$-alanine.

7. The method of claim 1, wherein the amine comprises a secondary amine.

8. The method of claim 7, wherein the secondary amine comprises at least one secondary amine selected from the group consisting of dimethylamine, diethylamine, methylethylamine, diisopropylamine, n-butylmethylamine, s-butylmethylamine, t-butylmethylamine, and dipropylamine.

9. The method for producing a 3-alkoxycarboxylic acid-N,N-disubstituted amide, the method comprising:
   reacting a carboxylic acid amide produced by the method of claim 1, with an alcohol.

* * * * *